(12) United States Patent
Roger et al.

(10) Patent No.: US 8,376,978 B2
(45) Date of Patent: Feb. 19, 2013

(54) OPTICAL ACCESS DISCONNECTION SYSTEMS AND METHODS

(75) Inventors: Rodolfo G. Roger, Clearwater, FL (US); Joel Tejedor, Largo, FL (US); Robert W. Childers, Trinity, FL (US)

(73) Assignees: Baxter International Inc., Deerfield, IL (US); Baxter Healthcare S.A., Glattpark (Opfikon) (CH)

( * ) Notice: Subject to any disclaimer, the term of this patent is extended or adjusted under 35 U.S.C. 154(b) by 873 days.

(21) Appl. No.: 11/673,395

(22) Filed: Feb. 9, 2007

(65) Prior Publication Data

US 2008/0195060 A1    Aug. 14, 2008

(51) Int. Cl.
*A61M 37/00* (2006.01)
(52) U.S. Cl. ............... 604/4.01; 604/65; 604/318
(58) Field of Classification Search ............ 604/318, 604/4.01–6.16, 65–67, 317; 600/485–490; 424/44–48
See application file for complete search history.

(56) References Cited

U.S. PATENT DOCUMENTS

| | | | |
|---|---|---|---|
| 3,618,602 A | 11/1971 | Shaw | |
| 3,864,676 A | 2/1975 | Macias et al. | |
| 4,010,749 A | 3/1977 | Shaw | |
| 4,181,610 A | 1/1980 | Shintani et al. | |
| 4,194,974 A | 3/1980 | Jonsson | |
| 4,294,263 A | 10/1981 | Hochman | |
| 4,295,475 A | 10/1981 | Torzala | |
| 4,399,823 A | 8/1983 | Donnelly | |
| 4,399,824 A | 8/1983 | Davidson | |
| 4,501,583 A | 2/1985 | Troutner | |
| 4,534,756 A | 8/1985 | Nelson | |
| 4,648,869 A | 3/1987 | Bobo, Jr. | |
| 4,661,096 A | 4/1987 | Teeple | |
| 4,710,163 A | 12/1987 | Butterfield | |
| 4,846,792 A | 7/1989 | Bobo et al. | |
| 4,982,742 A * | 1/1991 | Claude | 607/50 |
| 5,026,348 A | 6/1991 | Venegas | |
| 5,100,374 A | 3/1992 | Kageyama | |
| 5,139,482 A | 8/1992 | Simeon et al. | |
| 5,211,201 A | 5/1993 | Kamen et al. | |
| 5,454,374 A | 10/1995 | Omachi | |

(Continued)

FOREIGN PATENT DOCUMENTS

| CA | 2 175 903 | 5/1995 |
|---|---|---|
| CA | 2 282 628 | 11/2006 |

(Continued)

OTHER PUBLICATIONS

Canadian Office Action issued Jul. 11, 2012, corresponding to Canadian Appln. No. 2,673,574.

(Continued)

*Primary Examiner* — Tatyana Zalukaeva
*Assistant Examiner* — Benedict L Hanrahan
(74) *Attorney, Agent, or Firm* — K&L Gates LLP

(57) ABSTRACT

An access disconnection system includes: a material capable of absorbing blood from a patient upon an arterial or venous line disconnection; a light emitter positioned to emit light onto the material; a light receiver positioned to receive light reflected off of the material; and electronic circuitry operably coupled to at least one of the light emitter and receiver, the circuitry configured to provide an output (i) when light received by the receiver reaches a particular level or (ii) indicative of an amount of light received by the light receiver.

19 Claims, 15 Drawing Sheets

U.S. PATENT DOCUMENTS

| | | | |
|---|---|---|---|
| 5,509,822 | A | 4/1996 | Negus et al. |
| 5,674,390 | A | 10/1997 | Matthews et al. |
| 5,718,692 | A | 2/1998 | Schon et al. |
| 5,730,418 | A | 3/1998 | Feith et al. |
| 5,779,657 | A | 7/1998 | Daneshvar |
| 5,803,915 | A | 9/1998 | Kremenchugsky et al. |
| 5,813,432 | A | 9/1998 | Elsdon et al. |
| 5,911,706 | A | 6/1999 | Estabrook et al. |
| 5,931,801 | A | 8/1999 | Burbank et al. |
| 5,954,691 | A | 9/1999 | Prosl |
| 6,009,339 | A | 12/1999 | Bentsen et al. |
| 6,038,914 | A | 3/2000 | Carr et al. |
| 6,044,691 | A | 4/2000 | Kenley et al. |
| 6,077,443 | A | 6/2000 | Goldau |
| 6,090,048 | A | 7/2000 | Hertz et al. |
| 6,167,765 | B1 | 1/2001 | Weitzel |
| 6,206,851 | B1 | 3/2001 | Prosl |
| 6,208,880 | B1 | 3/2001 | Bentsen et al. |
| 6,221,040 | B1 | 4/2001 | Kleinekofort |
| 6,397,661 | B1 | 6/2002 | Grimes et al. |
| 6,402,207 | B1 | 6/2002 | Segal et al. |
| 6,406,460 | B1 | 6/2002 | Hogan |
| 6,461,329 | B1 | 10/2002 | Van Antwerp et al. |
| 6,500,154 | B1 | 12/2002 | Hakky et al. |
| 6,565,525 | B1 | 5/2003 | Burbank et al. |
| 6,572,576 | B2 | 6/2003 | Brugger et al. |
| 6,575,927 | B1 | 6/2003 | Weitzel et al. |
| 6,582,397 | B2 | 6/2003 | Alesi et al. |
| 6,585,675 | B1 | 7/2003 | O'Mahoney et al. |
| 6,595,942 | B2 | 7/2003 | Kleinekofort |
| 6,612,624 | B1 | 9/2003 | Segal et al. |
| 6,623,443 | B1 | 9/2003 | Polaschegg |
| 6,663,585 | B1 | 12/2003 | Ender |
| 6,752,785 | B2 | 6/2004 | Van Antwerp et al. |
| 6,827,698 | B1 | 12/2004 | Kleinekofort |
| 6,924,733 | B1 | 8/2005 | McTier et al. |
| 6,932,786 | B2 | 8/2005 | Giacomelli et al. |
| 6,979,306 | B2 | 12/2005 | Moll |
| 7,022,098 | B2 | 4/2006 | Wariar et al. |
| 7,040,142 | B2 | 5/2006 | Burbank |
| 7,052,480 | B2 | 5/2006 | Han et al. |
| 7,053,781 | B1 | 5/2006 | Haire et al. |
| 7,056,316 | B1 | 6/2006 | Burbank et al. |
| 7,060,047 | B2 | 6/2006 | Lodi et al. |
| 7,070,591 | B2 | 7/2006 | Adams et al. |
| 7,087,033 | B2 | 8/2006 | Brugger et al. |
| 2002/0198483 | A1 | 12/2002 | Wariar et al. |
| 2003/0009123 | A1 | 1/2003 | Brugger et al. |
| 2003/0036719 | A1 | 2/2003 | Giacomelli et al. |
| 2003/0126910 | A1 | 7/2003 | Burbank |
| 2003/0128125 | A1 | 7/2003 | Burbank et al. |
| 2003/0128126 | A1 | 7/2003 | Burbank et al. |
| 2003/0152482 | A1 | 8/2003 | O'Mahony et al. |
| 2003/0176829 | A1 | 9/2003 | Lodi et al. |
| 2003/0194894 | A1 | 10/2003 | Wariar et al. |
| 2003/0195453 | A1 | 10/2003 | Han et al. |
| 2003/0195454 | A1 | 10/2003 | Wariar et al. |
| 2004/0054352 | A1 | 3/2004 | Adams et al. |
| 2004/0113801 | A1 | 6/2004 | Gustafson et al. |
| 2004/0185709 | A1 | 9/2004 | Williams, Jr. et al. |
| 2004/0186409 | A1 | 9/2004 | Cavalcanti et al. |
| 2004/0186415 | A1 | 9/2004 | Burbank et al. |
| 2004/0201216 | A1 | 10/2004 | Segal et al. |
| 2004/0243046 | A1 | 12/2004 | Brugger et al. |
| 2005/0010118 | A1 | 1/2005 | Toyoda et al. |
| 2005/0010157 | A1 | 1/2005 | Baraldi et al. |
| 2005/0038325 | A1* | 2/2005 | Moll ............................ 600/300 |
| 2005/0096578 | A1 | 5/2005 | Kleinekofort |
| 2005/0131332 | A1 | 6/2005 | Kelly et al. |
| 2005/0230313 | A1 | 10/2005 | O'Mahony et al. |
| 2005/0241387 | A1 | 11/2005 | Miesel et al. |
| 2005/0245858 | A1 | 11/2005 | Miesel et al. |
| 2005/0256451 | A1 | 11/2005 | Adams et al. |
| 2006/0012774 | A1 | 1/2006 | O'Mahony et al. |
| 2006/0069339 | A1 | 3/2006 | Moll |
| 2006/0087120 | A1 | 4/2006 | Segal et al. |
| 2006/0116623 | A1 | 6/2006 | Han et al. |
| 2006/0130591 | A1 | 6/2006 | Perkins |
| 2006/0166548 | A1 | 7/2006 | Williams, Jr. et al. |
| 2006/0184087 | A1 | 8/2006 | Wariar et al. |

FOREIGN PATENT DOCUMENTS

| | | |
|---|---|---|
| CA | 2660537 A1 | 2/2008 |
| DE | 40 14 572 | 11/1991 |
| DE | 4014572 A1 * | 11/1991 |
| DE | 19802985 A1 | 7/1999 |
| EP | 0 259 551 | 9/1990 |
| EP | 0 472 798 | 3/1994 |
| EP | 1 401 518 | 3/2006 |
| GB | 2207749 A | 2/1989 |
| JP | 01250733 | 10/1989 |
| JP | 4-33860 | 4/1992 |
| JP | 2000131286 | 5/2000 |
| JP | 2006055588 | 3/2006 |
| JP | 2006110118 | 4/2006 |
| JP | 2007020738 | 2/2007 |
| JP | 2008503318 | 2/2007 |
| JP | 2007143895 | 6/2007 |
| JP | 2008-00219 | 1/2008 |
| WO | WO 81/00295 | 2/1981 |
| WO | WO 89/12228 | 12/1989 |
| WO | WO 95/12545 | 5/1995 |
| WO | WO 97/03712 | 2/1997 |
| WO | WO 97/10013 | 3/1997 |
| WO | WO 98/38485 | 9/1998 |
| WO | WO 99/12588 | 3/1999 |
| WO | WO 99/24145 | 5/1999 |
| WO | WO 01/47581 | 7/2001 |
| WO | WO 03/000315 | 1/2003 |
| WO | WO 03/006944 | 1/2003 |
| WO | WO 03/086504 | 10/2003 |
| WO | WO 03/086505 | 10/2003 |
| WO | WO 03/086506 | 10/2003 |
| WO | WO 2004/082740 | 9/2004 |
| WO | WO 2004/084972 | 10/2004 |
| WO | WO 2004/108192 | 12/2004 |
| WO | WO 2005/019416 | 3/2005 |
| WO | WO 2005/046439 | 5/2005 |
| WO | WO 2005/105199 | 11/2005 |
| WO | WO 2005/105200 | 11/2005 |
| WO | WO 2006/001759 | 1/2006 |
| WO | 2008/021462 A2 | 2/2008 |
| WO | PCT/US2008/051260 | 7/2008 |

OTHER PUBLICATIONS

Japanese Office Action issued Sep. 10, 2012, corresponding to Japanese Application No. 2009-549156.

* cited by examiner

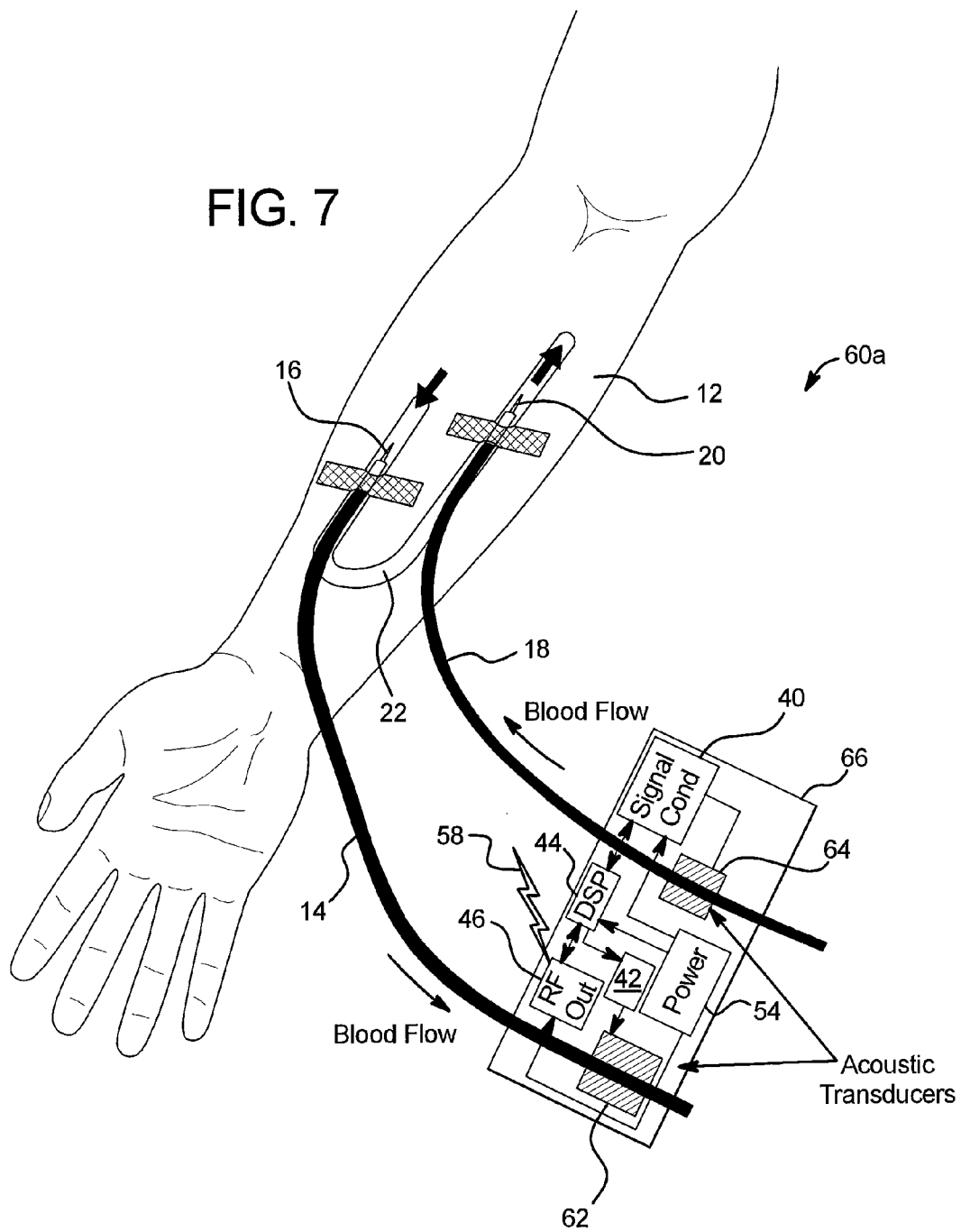

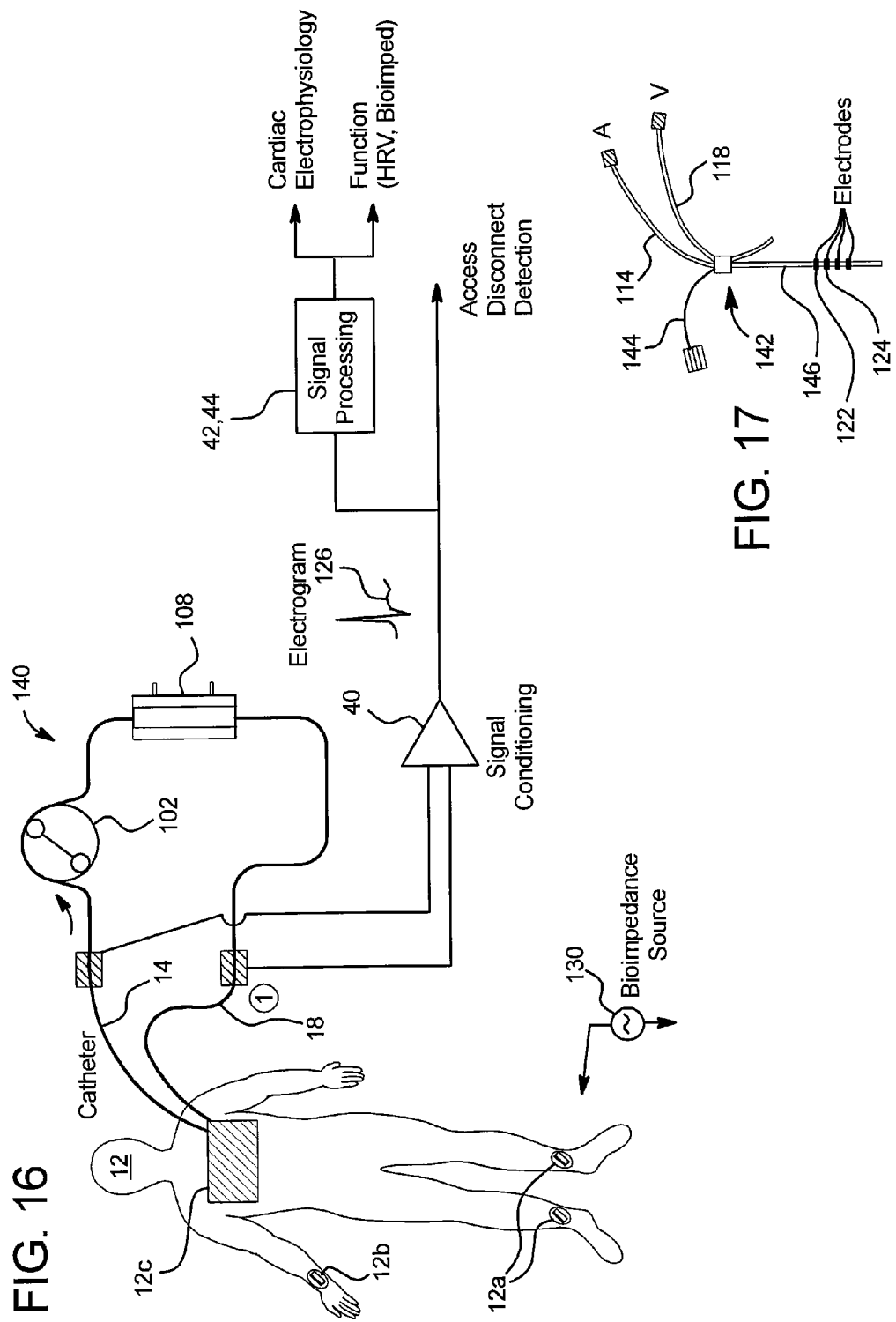

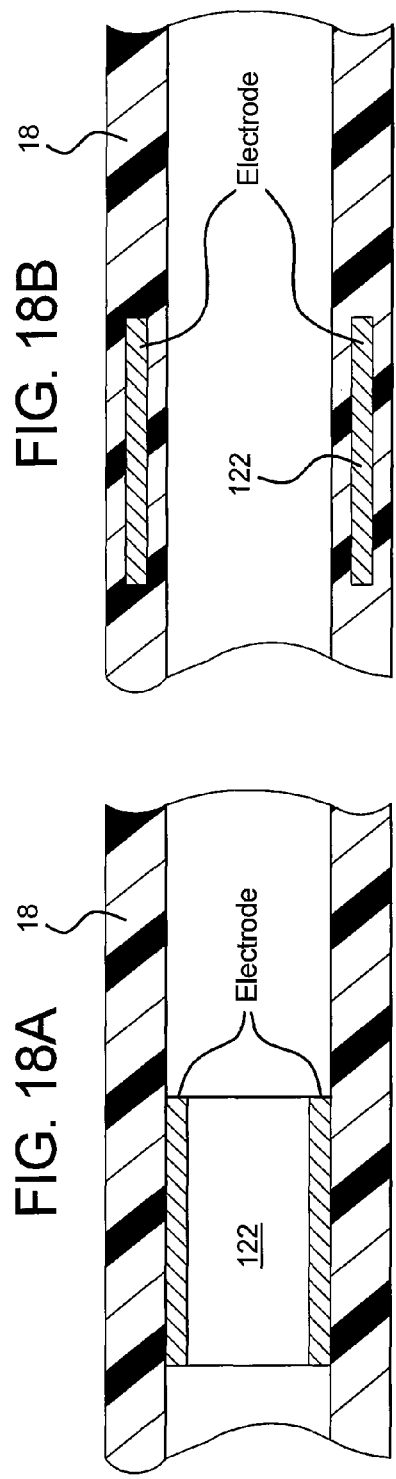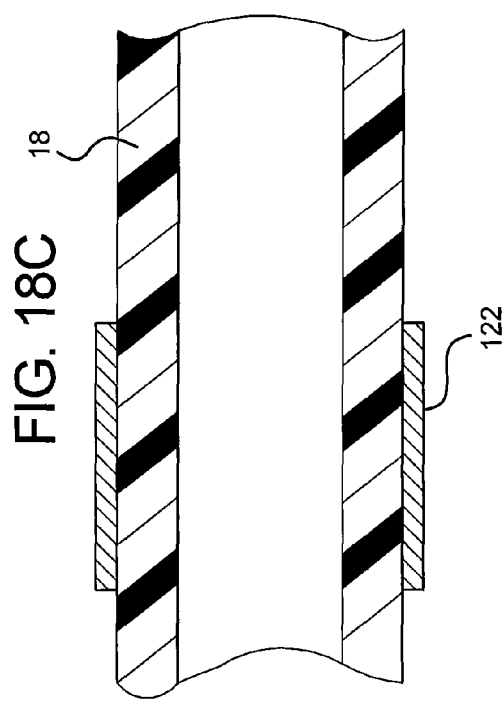

OPTICAL ACCESS DISCONNECTION SYSTEMS AND METHODS

BACKGROUND

The present disclosure relates generally to patient access disconnection systems and methods for medical treatments. More specifically, the present disclosure relates to the detection of a patient access disconnection, such as the detection of needle or catheter dislodgment during dialysis therapy.

FIG. 1 illustrates a known access disconnection configuration. Blood is drawn from an arm 12 of a patient through an arterial line 14 connected the patient via an arterial needle 16. Blood is returned to the patient, after it has been treated, via a venous line 18 and venous needle 20. Needles 16 and 20 actually connect to a shunt 22, which is placed in fluid communication with one of the patient's arteries and veins. Accidental disconnection of the arterial line 14 during treatment is not as serious an issue as this simply eliminates the source of blood to the blood pump. Access disconnection of venous line 18 during treatment is a serious concern because arterial line 14 keeps feeding blood to the blood pump, while venous line 18 returns blood to a location outside of the patient.

A variety of different medical treatments relate to the delivery of fluid to, through and/or from a patient, such as the delivery of blood between a patient and an extracorporeal system connected to the patient via a needle or needles inserted within the patient. For example, plasmapherisis, hemodialysis, hemofiltration and hemodiafiltration are all treatments that remove waste, toxins and excess water directly from the patient's blood. During these treatments, the patient is connected to an extracorporeal circuit and machine, and the patient's blood is pumped through the circuit and machine. Waste, toxins and excess water are removed from the patient's blood, and the blood is infused back into the patient.

In these treatments, needles or similar access devices are inserted into the patient's vascular system so that the patient's blood can be transported to and from the extracorporeal machine. Traditional hemodialysis, hemofiltration and hemodiafiltration treatments can last several hours and are generally performed in a treatment center about three to four times per week. In in-center treatments, patients undergoing hemodialysis, for example, are monitored visually to detect needle dislodgment. However, the needle may not be in plain view of the patient or medical staff (e.g., it may be covered by a blanket) such that it could delay detection and timely response.

Moreover, in view of the increased quality of life, observed reductions in both morbidity and mortality and lower costs with respect to in-center treatments, a renewed interest has arisen for self-care and home therapies, such as home hemodialysis. Such home therapies (whether hemodialysis, hemofiltration or hemodiafiltration) can be done during the day, evening or nocturnally. If unsupervised or asleep, dislodgment risks increase because a caregiver is not present and perhaps even the patient is not aware of a dislodgment.

Various systems exist for detecting needle dislodgement in hemodialysis. For example, U.S. Pat. No. 7,022,098 ("the '098 Patent") and U.S. Pat. No. 7,052,480 ("the '480 Patent"), both entitled Access Disconnection Systems And Methods, and assigned to the eventual assignee of the present application, disclose access disconnection systems that measure an electrical impedance of the extracorporeal dialysis circuit connected to the vascular access needles. An external voltage or current source is used to inject a small current (e.g., less that 2.5 µ-Amp) into the blood flow. While this external current is small compared to other systems, the source still requires that measures be taken to ensure that the current does not exceed 10 µ-Amp, which is considered in the art to be a safety limit for intercardiac devices. Further, sensitivity of the impedance system can be decreased when the patient is connected to earth ground (e.g., through grounding devices found in clinics and homes).

Another problem with systems that inject current into the extracorporeal circuits occurs if the dislodged needle reestablishes contact with the other needle through leaked blood. Here, the electrical parameter being sensed, e.g., impedance, may not change or not change enough to signal an access disconnection even though one has occurred.

A further obstacle involves the addition of contacts to the disposable portion of the blood treatment system. Metal or otherwise conductive members placed in the disposable add a certain amount of manufacturing difficulty and cost.

A need accordingly exists for improved blood access disconnection systems.

SUMMARY

The examples described herein disclose access disconnection systems and methods applicable for example to: plasmapherisis, hemodialysis ("HD"), hemofiltration ("HF") and hemodiafiltration ("HDF"). The access disconnection systems may also be used with continuous renal replacement therapy ("CRRT") treatments requiring vascular access. The access disconnection examples below operate with systems having a diffusion membrane or filter, such as a dialyzer, e.g., for HD or HDF, or a hemofiliter, e.g., for HF.

Moreover, each of the systems described herein may be used with clinical or home setting machines. For example, the systems may be employed in an in-center HD, HF or HDF machine, which runs virtually continuously throughout the day. Alternatively, the systems may be used in a home HD, HF or HDF machine, which is run at the patient's convenience. One such home system is described in U.S. Pat. No. 8,029,454 ("the '454 Patent"), entitled "High Convection Home Hemodialysis/Hemofiltration And Sorbent System," filed Nov. 4, 2004, assigned to the eventual assignee of the present patent, the entire contents of which are incorporated herein expressly by reference.

The access disconnection examples below operate with systems having a dialysate (infusate) supply, which can be a single bag or multiple bags of dialysate supply ganged together and used one after another. Further alternatively, each of the access disconnection systems shown below can be used with a machine having an on-line source, such as one or more concentrate pump configured to combine one or more concentrate with water to form dialysate on-line. On-line sources are used commonly with HD systems for example.

Various non-invasive access disconnection systems are described herein. The systems by and large do not inject a voltage or current into the patient. This illuminates problems with patient grounding inherent in current inducing systems. Because the systems do not rely on the connection or disconnection of an electrical loop, they tend to be immune from the reestablishment of a conductive path with a dislodged needle and lost blood. The disclosed systems in various embodiments communicate with the dialysis machine wirelessly, e.g., through a radio frequency signal. In this manner, the systems do not add to the disposable tubing and/or cassette that the machine uses, increasing manufacturing feasibility and reducing cost.

A first system uses a piezoelectric or electromagnetic transducer (referred to hereafter generally as piezoelectric for convenience) operating for example in the Mega-Hertz frequency range, which transmits ultrasound waves into tissue. The transducer's body is parallel to the tissue in one embodiment while the piezoelectric itself is at an angle to produce ultrasound components aligned with blood flow direction.

Red cells in the blood stream act as reflectors for the ultrasound, echoing the wave back into the transducer. Another piezoelectric or electromagnetic crystal (referred to hereafter generally as piezoelectric for convenience) can be used to receive the echoes. Ultrasound frequency is changed as the wave reflects on the blood cells via the Doppler effect. The changes in frequency of the ultrasound signal are an indication of the speed of the reflecting cells. The first system processes the received echoes and extracts flow rate information.

The first system as mentioned uses a piezoelectric transmitter and a piezoelectric receiver or a single transducer that performs both functions. Electronic circuitry is connected to the transducers or transducer to produce the excitation signals and to process the echoes. In one implementation, the electronics also include a radio frequency ("RF") link to the hemodialysis instrument. Once the treatment has started, the ultrasound device gathers information from the blood stream. Peak speed of reflectors, pulsatile characteristics of the blood flow, turbulence in the access are some of the parameters that are monitored as described in more detail below. The access disconnection system exchanges such information with the dialysis instrument via the RF link. Venous needle dislodgement will necessarily introduce a radical change in the sensed parameters, allowing access disconnect detection.

In one implementation of the first access disconnection system, the ultrasound transducer is held in place with a band via a hook and loop assembly, magnetic coupling or other buckle mechanism. The band offers tube restraining to mechanically prevent needle dislodgement.

A second access disconnection system uses the propagation properties of sound in blood within the extracorporeal circuit to determine for example if the venous section of the extracorporeal circuit is connected to the patient. The second system uses at least one acoustic transducer, which generates a sound wave signal that is processed by the dialysis unit, which has access to other parameters of the treatment such as blood flow, dialysis flow, valve sequencing etc. The sound waves can be sonic, subsonic or a pressure wave emitted into the blood stream. The signals can be of any suitable frequency, could be a single frequency or multiple frequencies, it could be continuous, pulsed, modulated in amplitude, frequency or phase. The acoustic transducer can be piezoelectric, electromagnetic or any suitable type capable of converting electrical excitation into pressure waves and/or vice versa.

The second access disconnection system can be implemented in at least three ways. One implementation uses two acoustic transducers, one coupled to the venous section of the extracorporeal circuit, while the other is coupled to the arterial section of the extracorporeal circuit. One of the transducers transmits an acoustic signal into the blood stream, while the other transducer receives the signal. If any of the sections becomes disconnected, the receiver no longer detects the emitted signal, triggering an alarm. The dual acoustic transducers can each perform both functions, transmit and receive, making possible an embodiment in which the dual transducers switch functions with each other.

A second implementation uses either one acoustic transducer, doubling as transmitter and receiver, or two transducers, one dedicated to transmit and the other to receive. Here, both emitter and receiver are coupled to the venous section of the extracorporeal circuit. In this implementation the transmitter sends an acoustic pulse into the blood. The pulse reflects in the extracorporeal circuit interface producing a signature response. The system monitors, processes and analyzes the signature of the echo produced when the venous line is connected and yields a baseline acoustic signature response. The acoustic signature response produced when the venous line is disconnected is different from the stored pattern. Processing of the received signal detects such change and generates an alarm, pump and/or valve shutdown or occlusion as desired.

A third implementation of the second access disconnection system uses passive sonar. The blood stream in the extracorporeal circuit is subjected to a series of operations that introduce acoustic waves into it. Blood pump, drip chamber, interaction with the dialyzer and the patient each create an acoustic pattern. This sound pattern constitutes an acoustic signature, e.g., in the venous line when the needle is lodged, will be different from the one when it is dislodged. The passive sonar implementation uses an acoustic transducer coupled to the venous line, which acts as a receiver. The receiver transducer monitors, processes and analyzes acoustic signals in the blood to create a baseline acoustic signature. When the pattern changes due to a venous needle dislodgement, the processing of the received signal detects this change and generates an alarm, etc.

A third access disconnection/ blood leak detection system uses optical sensors. It is not uncommon that a small blood leak is present around the areas at which the access needles connect to the patient's arm. This effect, however, should be limited to a small area around the access points. If the blood leak extends to a larger area, it likely indicates needle partial or full dislodgement, which must be addressed immediately.

The optical system in one embodiment uses a flexible circuit having distributed optically reflective sensors. Here, flexible circuit wraps around the arm of the patient in one embodiment. In another implementation, the optical system incorporates either a rigid or semi-rigid circuit mounted on a flexible arm band made of plastic, rubber or cloth, for example. The arm band can also be disposable. In any case, the attachment mechanism can be sized and configured to be attached alternatively for blood access with another body area, such as a patient's leg, or for catheter access, e.g., in the patient's neck.

The flexible circuit can be in contact with a piece of gauze covering the needle recess. For sterility the contact surface is cleaned with a disinfectant. Alternatively, the contact area is covered with a sterile disposable transparent film, which can be self-adhesive. The film is discarded after the treatment is completed.

The flexible circuit can be attached to the patient using a hook and loop type of mechanism, magnetic straps, magnetic buckle or other type of releasably securable and cleanable apparatus.

The reflective optical sensors in one embodiment use of a light emitting diode, such as a light source, and a photocell or phototransistor, as receiver. The emitted light has a wavelength that has is chosen so that the color of blood absorbs its energy. As long as the light illuminates a white gauze, a percentage of the light's energy is reflected towards the receiver. On the other hand, if blood on the gauze absorbs most of all of light energy, the receiver detects a considerable loss of signal and signals or alarm, etc.

A local micro-controller in one embodiment gathers data from the optical sensors and reports this data via, e.g., a radio frequency link, to the dialysis instrument. In one implementation, the micro-controller remains in a sleep mode or power-save mode, which turns the optical sensors off until the dialysis instrument requests data via the radio frequency link. The micro-controller then "wakes up", energizes the light sources, reads the optical receivers and transmits the status back to the dialysis instrument. If one (or perhaps more than one) of the sensors does not receive enough light, the processor issues a distress call and, additionally or alternatively, energizes an audible alarm. The machine takes any other appropriate action, such as shutting down a pump or clamping a line or valve.

In a fourth access disconnection embodiment, the dialysis system uses the patient's cardiovascular electrical system to detect an access disconnection. Humans have an internal electrical system that controls the timing of heartbeats by regulating: heart rate and heart rhythm. Generally, the body's electrical system maintains a steady heart rate of sixty to one hundred beats per minute at rest. The heart's electrical system also increases this rate to meet the body's needs during physical activity and lowers it during sleep.

In particular, the heart's electrical system controls the timing of the body's heartbeat by sending an electrical signal through cells in the heart, namely, conducting cells that carry the heart's electrical signal and muscle cells that enable the heart's chambers to contract. The generated electrical signal travels through a network of conducting cell pathways by means of a reaction that allows each cell to activate the one next to it, passing along the electrical signal in an orderly manner. As cell after cell rapidly transmits the electrical charge, the entire heart contracts in one coordinated motion, creating a heartbeat.

The system of the present disclosure uses an electrocardiogram or electrogram ("ECG") setup. In one implementation, a first electrode is attached to the venous line and a second electrode is attached to the patient. The electrodes are connected electrically to signal conditioning circuitry. The signal conditioning circuitry produces ECG signals when the arterial and venous connections are made properly. When a partial or complete access disconnection occurs with either the arterial or venous needles, electrical communication with the body's electrical system through the extracorporeal path is lost as is the ECG signal. Additional circuitry detects this dropout and sends an access disconnection signal to the blood treatment machine.

Alternative ECG embodiments include the attachment of both first and second electrodes to the extracorporeal circuit. Also, blood access can be made at or close to the patient's heart, increasing sensitivity to the ECG signals, as opposed to access at the patient's arm. To that end, disclosed herein is an embodiment for a dialysis needle equipped with the electrodes used for accessing the patient's blood at or near the heart. Also disclosed herein are various embodiments for tubing having electrodes implanted either inside the tubing, within the tubing or outside the tubing. Depending on the electrode configuration, the electrodes communicate electrically with the blood directly, capacitively, inductively, or wirelessly, e.g., through radio frequency.

The ECG system is also adaptable for other uses besides the detection of vascular access disconnection. The ECG signals may be further processed to calculate other physiological parameters such as heart rate variability, respiration, stroke volume, cardiac output and central blood volume. To this end, an electrical source can be added to the ECG system to measure bioimpedance. Further, a solution can be injected into the patient's body to assist in one or more of the above parameters. The ECG system can also be used to assist control of patients with heart rhythm management devices (pacemakers) via cardiac electrophysiology measurements to change cardiovascular parameters beneficially during dialysis.

In a fifth system, a blood leak device using capacitive sensors is provided. The device includes outer layers of insulation, e.g., plastic layers. Inside, the device includes an array of capacitors. A layer of shielding is also provided inside the shielding. If a blood leak develops beneath the capacitive device, the region of capacitors sensing a dielectric change grows. If the region stops growing, a system using the capacitive device assumes a normal amount of seepage has occurred, which is distinguishable from a blood leak or needle dislodgement. If the blood leak grows large enough, the system using the capacitive device assumes that a partial or full access disconnection has occurred and causes an alarm.

In any of the above described access disconnection embodiments, the circuitry for the access disconnection systems can be located locally at the patient or sensing site, remotely within the machine, or some combination thereof. Depending on the location of the circuitry, the signal sent from the access disconnection system to the dialysis machine can be a steady, e.g., conditioned digital signal, an intermittent signal, a signal sent on command or some combination thereof. The signal can be sent via wires or wirelessly.

Further, any of the above described access disconnection/blood leak detection embodiments can be used alternatively in a redundant system with another, different type of access disconnection/blood leak system. For example, any system that looks for an electrical connection to be broken (described loosely as an access disconnection system for ease of description but in know way intending to limit the meaning of the term) can be combined with a system that looks for an electrical connection to be made (described loosely as a blood leak detection system for ease of description but in know way intending to limit the meaning of the term) to capitalize on benefits inherent with each type of system.

It is therefore an advantage of the present disclosure to provide an improved access disconnection system for blood treatment machines.

It is another advantage of the present disclosure to provide non-invasive access disconnection systems.

It is a further advantage of the present disclosure to provide access disconnection systems that do not induce current into the patient's blood.

It is still another advantage of the present disclosure to provide access disconnection systems that do not add to disposable cost or manufacture.

It is still a further advantage of the present disclosure to provide access disconnection systems that circumvent problems from to electrical reconnection due to lost blood.

It is yet another advantage of the present disclosure to provide an access disconnection system that yields other valuable blood parameter information.

It is yet a further advantage of the present disclosure to provide access disconnection systems that are compatible with blood needle and catheter applications.

Additional features and advantages are described herein, and will be apparent from, the following Detailed Description and the figures.

BRIEF DESCRIPTION OF THE FIGURES

FIG. 7 is a perspective view showing one embodiment of an acoustic access disconnection system, which employs two acoustic transducers.

FIG. 16 is a schematic view of another embodiment of a system that uses electrocardiogram ("ECG") signals to detect an access disconnection.

FIG. 17 is a plan view of one embodiment for a cardiac catheter used with the ECG system of FIG. 16.

FIGS. 18A to 18C illustrate various embodiments for coupling an electrical contact with the patient's blood, the embodiments capable of being used with the systems of FIGS. 16 and 17.

DETAILED DESCRIPTION

The examples described herein are applicable to any medical fluid therapy system requiring vascular access. The examples are particularly well suited for the control of kidney failure therapies, such as all forms of hemodialysis ("HD)"), hemofiltration ("HF"), hemodiafiltration ("HDF") and continuous renal replacement therapies ("CRRT") requiring vascular access.

Ultrasound Remote Access Disconnection Sensor

Figure 1:
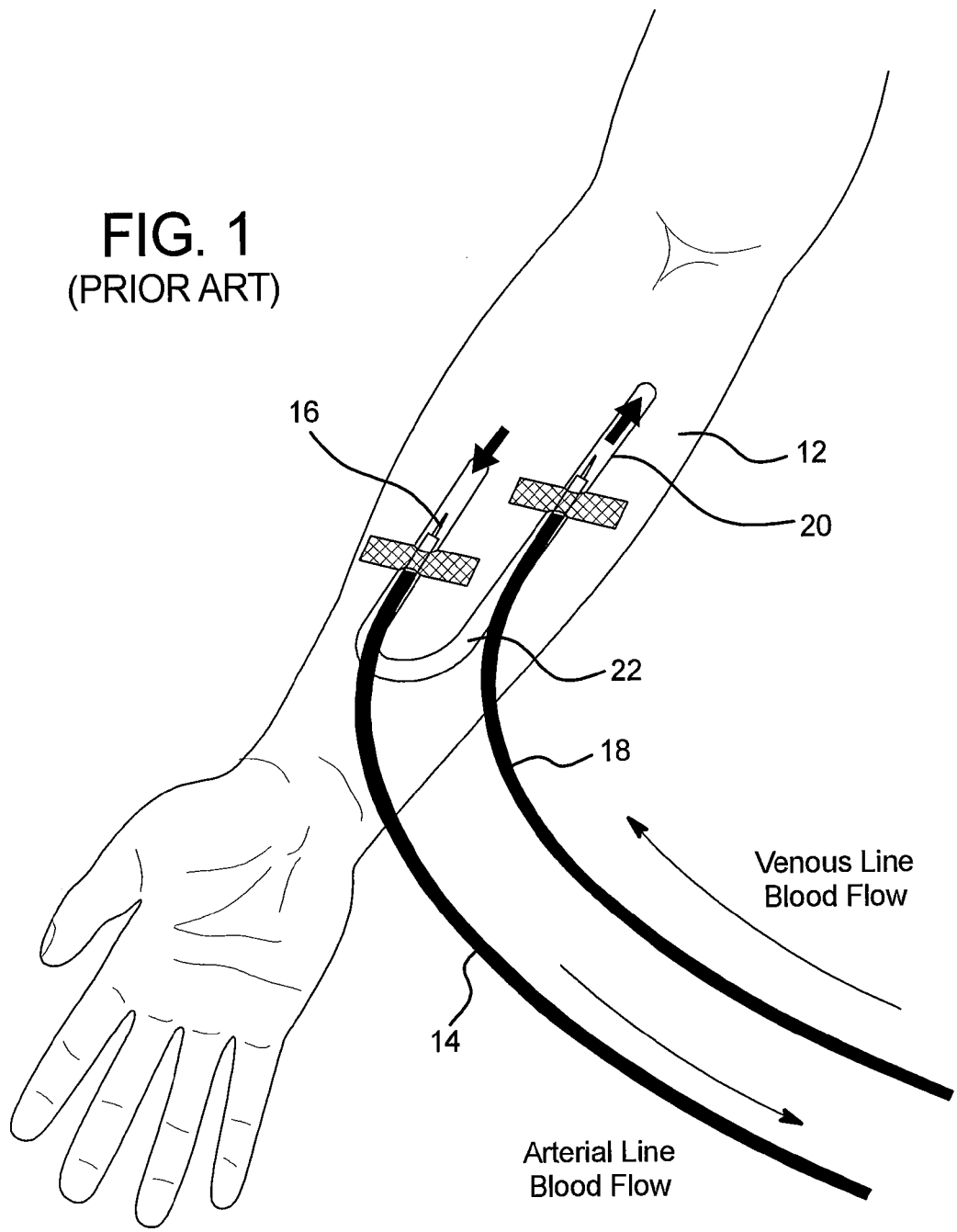
FIG. 1 illustrates a known arterial and venous access configuration.
Figure 2:
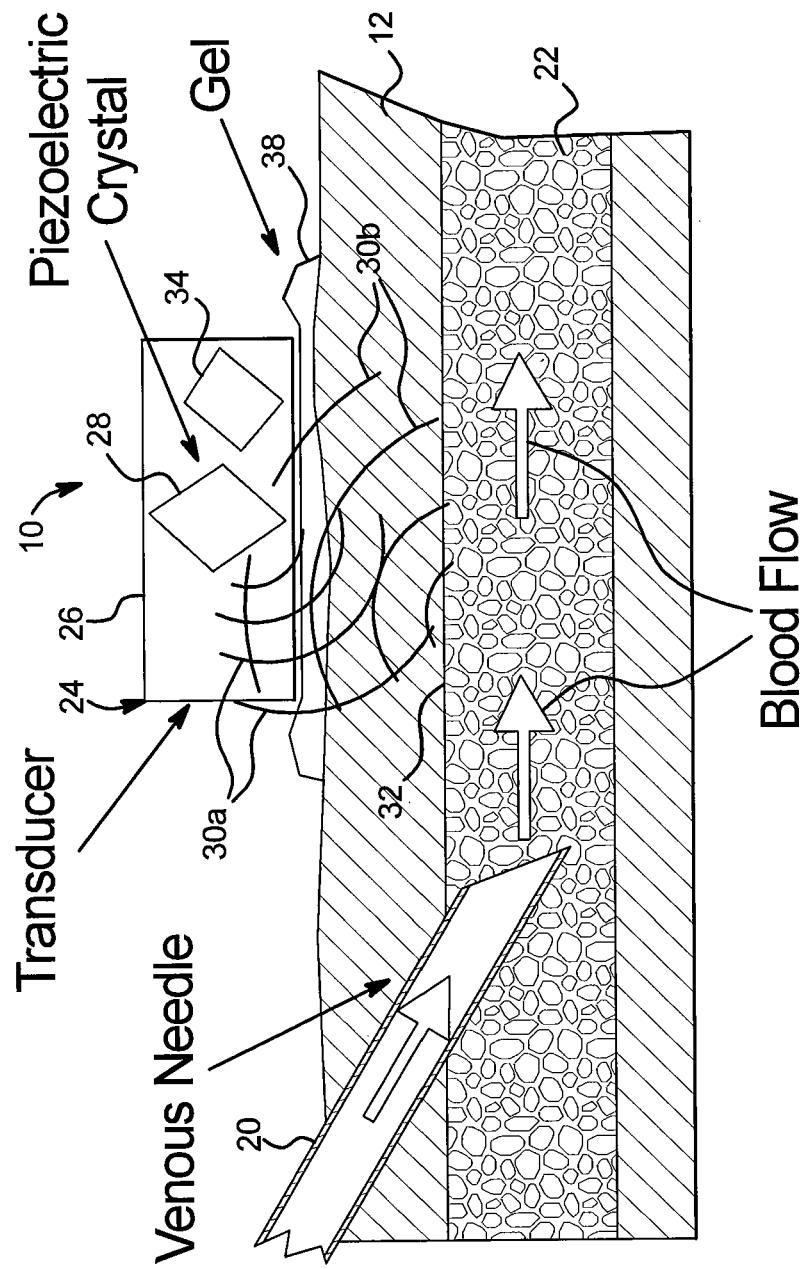
FIG. 2 is a sectioned elevation view showing one embodiment of an access disconnection system using ultrasound.
Figure 3:
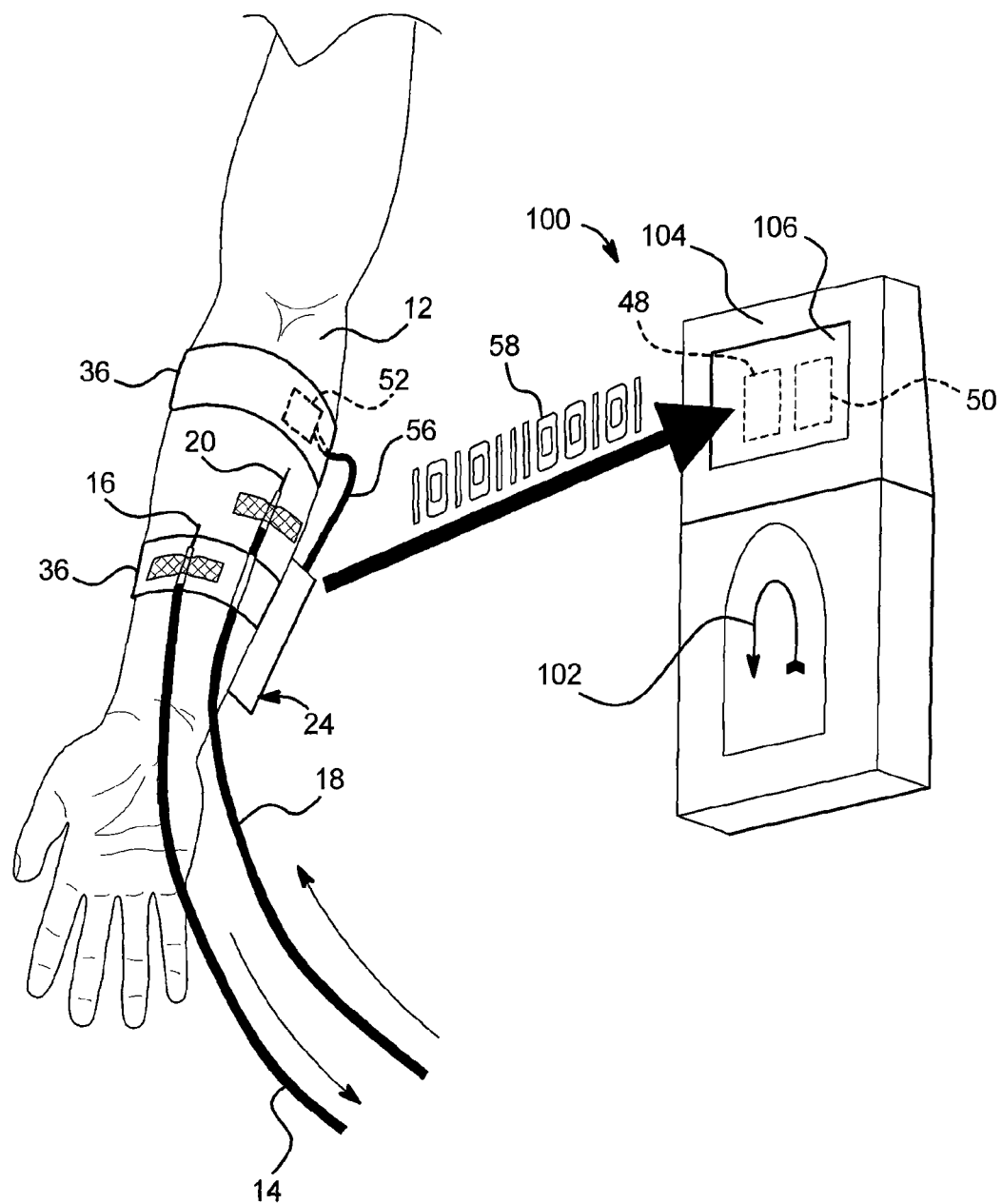
FIG. 3 is a perspective view showing the system of FIG. 2 and one embodiment for it to communicate with a blood treatment machine.
Figure 4:
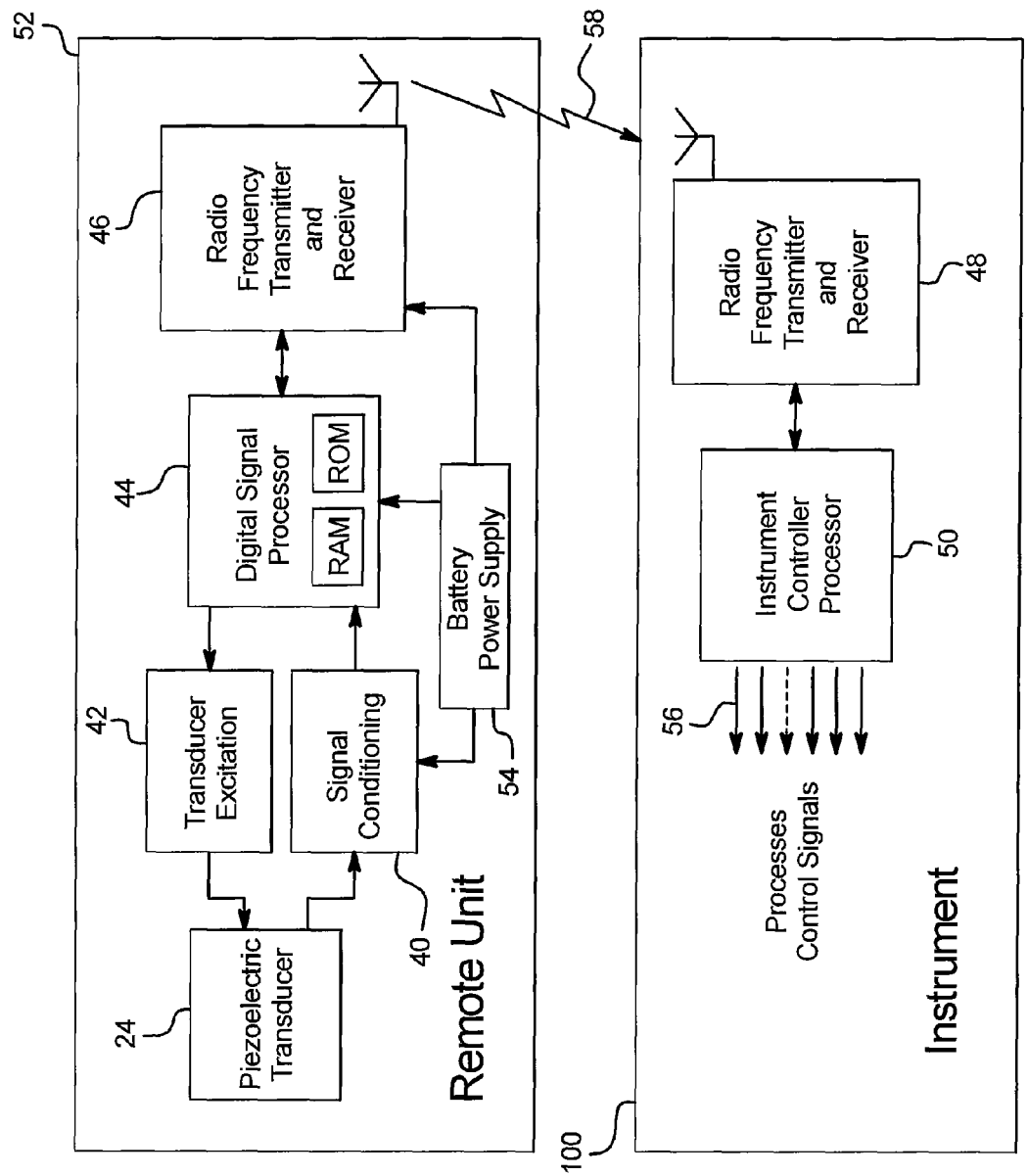
FIG. 4 is a schematic view of one embodiment of the electronics associated with the system of FIG. 2.
Figure 5:
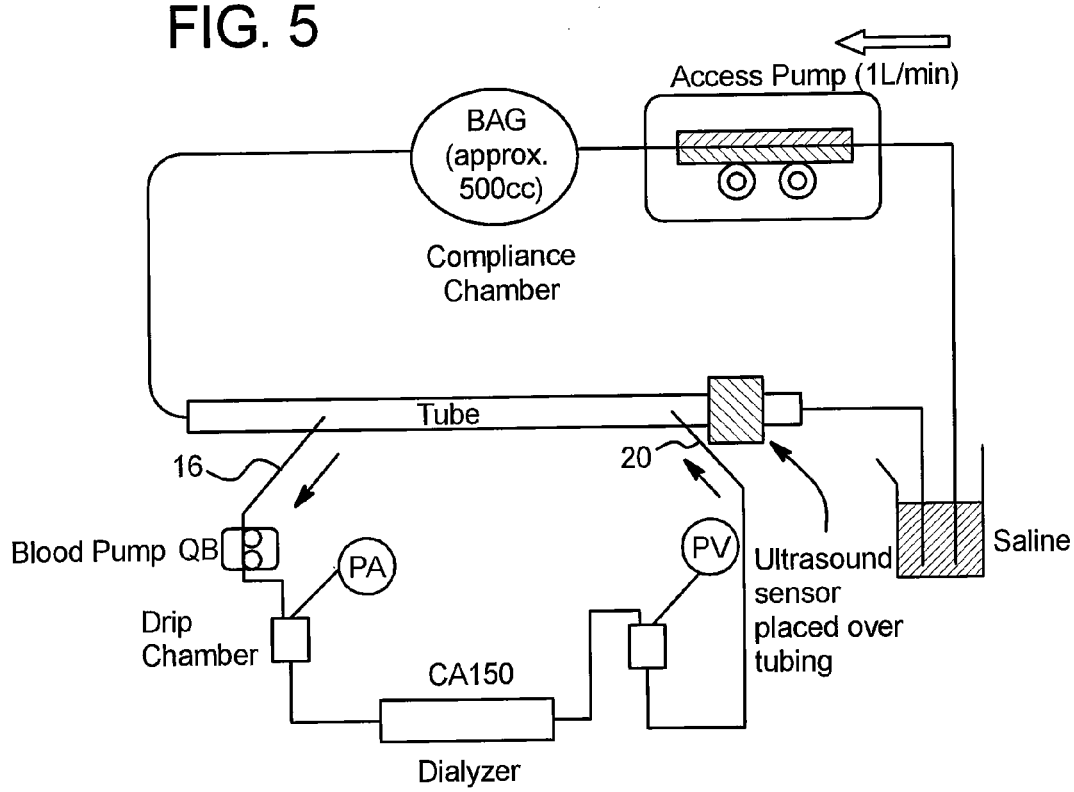
FIG. 5 is a schematic view of one simulation of the ultrasound access disconnection system of FIG. 2.
Figure 6:
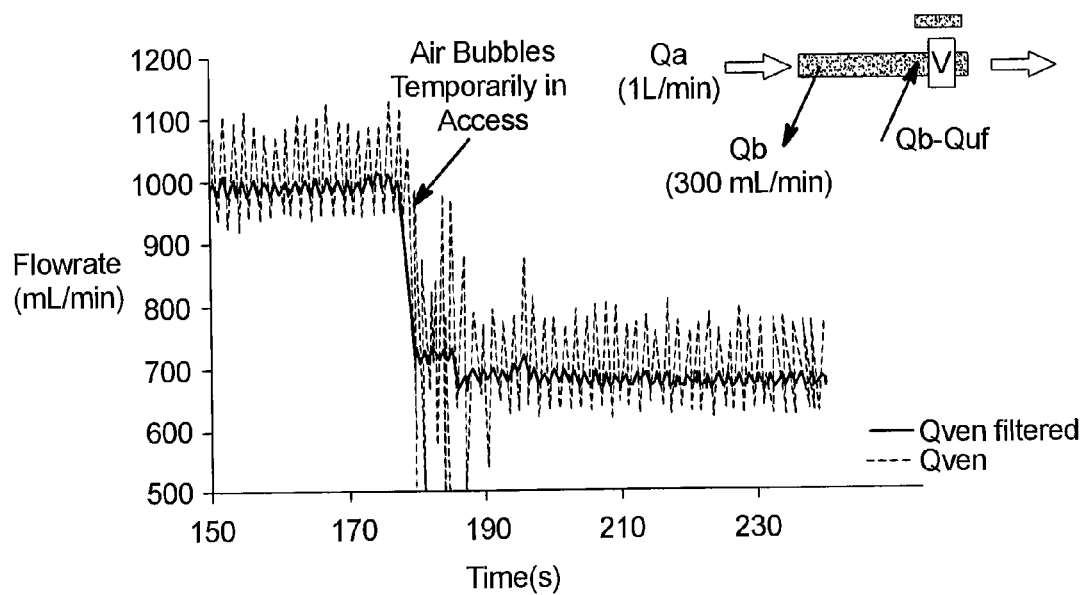
FIG. 6 is a chart illustrating results from testing done on the simulation of FIG. 5.

Referring now to the drawings and in particular to FIGS. 2 to 4, an ultrasound access disconnection system 10 is illustrated. FIG. 2 shows the details of system 10. FIG. 3 shows one apparatus for attaching system 10 to patient 12. FIG. 3 also shows one embodiment for interfacing system 10 with blood treatment or dialysis machine 100. While system 10 refers generally to the remote apparatus connected to the patient as seen in FIG. 2, system 10 and indeed each of the systems described herein also includes the machine or instrument, such as a dialysis machine. FIG. 4 shows an embodiment of the electronics (either onboard or remote electronics) associated with system 10. FIGS. 5 and 6 provide test results.

Any of the vascular disconnection examples described herein, including system 10, is operable with machine 100, which can include a diffusion membrane or filter, such as a dialyzer, e.g., for HD or HDF, or a hemofilter, e.g., for HF. Moreover, machine 100 and any of the access disconnection systems described herein may be used in clinical or home settings. For example, machine 100 and the access disconnection systems may be employed in an in-center HD machine, which runs virtually continuously throughout the day. Alternatively, they may be used in a home HD machine, which can for example be run at night while the patient is sleeping.

Machine 100 in one embodiment has a dialysate (infusate) supply. Alternatively, multiple bags of dialysate supply are ganged together and used one after another. In such a case, the emptied supply bags can serve as drain or spent fluid bags. Further alternatively, machine 100 can be used with an on-line source, such as one or more concentrate pump configured to combine one or more concentrate with water to form dialysate on-line. On-line sources are used commonly with HD systems for example.

Although not illustrated, machine 100 can operate with an in-line or batch heater that heats the dialysate or infusate to a desired temperature. The heater can be located upstream or downstream of a fresh supply pump for example. Machine 100 includes a dialysate air trap, which can be located at or near the heater to capture air egression from the dialysate due to heating. Likewise, the extracorporeal circuit operable with blood pump 102 also includes one or more air detector and air removal apparatus (e.g., air trap).

HD, HF, HDF or CRRT machine 100 also includes blood pumping systems, shown below, which are known generally in the art, e.g., the use of one or more peristaltic blood pump. HD, HF, HDF or CRRT machine 100 also includes dialysate proportioning systems, mentioned above, which are also known and need not be described here. The '534 Patent, incorporated herein by reference, describes a proportioning system for example.

Machine 100 also includes an apparatus and method for knowing how much dialysate has been used for clearance and how much ultrafiltration volume has been removed. This apparatus controls and knows how much ultrafiltrate has been removed from the patient and controls the flowrate of dialysate to and from the dialyzer, extracorporeal circuit and/or hemofilter. The apparatus also ensures that the necessary amount of ultrafiltrate is removed from the patient by the end of treatment.

Machine 100 includes an enclosure 104 as seen in FIG. 3. Enclosure 104 varies depending on the type of treatment, whether the treatment is in-center or a home treatment, and whether the dialysate/infusate supply is a batch-type (e.g., bagged) or on-line. An in-center, on-line enclosure 104 tends to be bigger and more robust due to the additional dialysate producing equipment and the frequency of use of such machines. A home therapy enclosure 104 is desirably smaller and built so that machine 100 can be moved about one's home or for travel.

FIG. 2 illustrates that system 10 includes a transducer 24. Transducer 24 in the illustrated embodiment includes a housing 26, which houses a piezoelectric crystal 28. Transducer 24 transmits power from one type of system to another. In the piezoelectric embodiment, transducer 24 power is provided in the form of electricity from a piezoelectric material acted upon. System 10 includes a transducer excitation apparatus 42 as seen in FIG. 4, which applies an electrical field to piezoelectric crystal 28. Piezoelectric crystal 28 undergoes mechanical deformation due to the electric field. In this manner, crystal 28 is induced to resonate (vibrate) at a certain frequency to produce ultrasonic waves. In an embodiment, the ultrasonic waves are produced in the Mega-Hertz frequency range. A layer of gel couples the waves to the patient in one embodiment. The ultrasound waves in the presence of human tissue travel through the tissue to a depth that depends on the power and frequency of the excitation.

Housing 26 of transducer 24 in the illustrated embodiment is positioned in parallel with the arm and tissue of patient 12. Crystal 28 on the other hand is placed at an angle, e.g., forty-five degrees, relative to the arm and tissue of patient 12 to produce ultrasound waves 30*a* having directional components both aligned with and perpendicular to the direction of blood flow.

Blood cells 32, e.g., red blood cells, within the blood stream serve as reflectors for the ultrasound waves, echoing waves 30*b* back towards a second piezoelectric crystal 34. It should be appreciated however that first piezoelectric crystal 28 could perform both emitter and receiver functions, in which case second crystal 34 is not needed. In the illustrated embodiment, receiver crystal 34 is located in the same housing 26 of the same transducer 24 as is emitter crystal 28. Alternatively, receiver crystal 34 is located in a separate transducer housing. In the illustrated embodiment, receiver crystal 34 is also mounted at an angle, e.g., forty-five degrees, relative to the arm and tissue of patient 12.

For receiver piezoelectric crystal 34, reflected waves 30*b* apply mechanical stress to receiver crystal 34, causing crystal 34 to become electrically charged and to vibrate at its resonant frequency creating an ultrasound wave. The reflected ultrasound waves 30*b* have a different frequency than do the emitted ultrasound waves 30*a*, an effect known as the Doppler effect. The change in frequency is dependent on the speed and direction of movement of blood cells 32 flowing though the access site. The electronics in system 10 stores software that processes the received echoes 30*b* to determine blood parameters, such as, blood flowrate of the red blood cells, peak flowrate of the reflectors, changes in blood flowrate, e.g., pulsatile characteristics of the blood flow, turbulence in the access line as described in more detail below.

In the embodiment illustrated in FIG. 3, transducer 24 and the electronics described below are held in place via bands 36. Bands 36 have suitable fasteners, such as Velcro™ fasteners or other type of frictionally engaging fastener, buttoned or snap-fitted fastener. Bands 36 serve a second function, namely, FIG. 2 shows that band 36 holds transducer 24 against patient 12 via a gel 38. Gel 38 couples the ultrasound wave into the patient's tissue.

FIG. 4 shows an embodiment of the electronics associated with system 10. A digital signal processor ("DSP") 44, which can include onboard random access memory ("RAM") and read only memory ("ROM"), sends an output signal to transducer excitation appratus 42. Excitation apparatus 42 excites emitter crystal 28 of transducer 24 as described above. Reflected waves 30*b* cause receiver crystal 34 (or crystal 28 operating as both emitter and receiver) to vibrate and create an ultrasound wave, which is sent to signal conditioning 40. Signal conditioning 40 in one embodiment includes an analog to digital ("A/D") converter, which digitizes the reflected wave into a form that DSP 44 can process. Signal conditioning 40 may, in another embodiment, contain demodulation circuitry to separate the signal components in a manner useful for Doppler calculations, for example.

DSP using onboard software in one embodiment detects a flow or access condition, a no-flow or full-access disconnection condition or a partial-flow or partial access diconnection condition. DSP 44 also uses the conditioned signals to detect blood flowrate, e.g., by equating a particular frequency to a particular blood flowrate. The correlation can be determined empirically and checked for repeatability. A peak frequency corresponds to peak blood flowrate. DSP 44 also detects changes in blood flowrate even when they do not rise to the level indicating an access disconnection. This information can be used to determine blood flow turbulence for example, which in turn can be used for example diagnostically to monitor or determine therapy efficiency or effectiveness.

DSP 44 communicates back and forth with a remote or wireless emitter/receiver 46, such as a radio frequency ("RF") emitter/receiver. Other remote signals may be used alternatively, such as a microwave signal. Further alternatively, system 10 is hard-wired to machine 100 and communicates via electrical signals, e.g., 4 to 20 mA or 0 to 5 VDC signals.

Machine 100 includes a wireless transmitter/receiver 48, such as an RF transceiver. In system 10, communicator 48 instrument 100 sends messages to and receives messages from the remote unit via communicator 46. Communicator 48 in turn communicates back and forth with a central processing unit ("CPU") 50 located within 100. CPU 50 in an embodiment includes a supervisory processor that communicates via signals 56 with one or more delegate processor and circuit board or controller located within machine 100. Transducer 24, signal conditioning 40, excitation apparatus 42, DSP 44 and emitter 46 are located on a printed circuit board ("PCB") 52 in the illustrated embodiment. PCB 52 can be located within transducer housing 26, within a separate housing (not illustrated), or within a housing that also houses one or more transducer 24. In an alternative embodiment, DSP 44 and its associated functionality are located and performed, respectively, at CPU 50 of machine 100.

PCB 52 also includes a battery, a power supply or a combination of both, referred to generally herein as power supply 54. Supply 54 can be a rechargeable battery, for example. Supply 54 powers the components of PCB 52, such as, signal conditioning, DSP 44 and wireless communicator 46. Power supply 54 is rechargeable in an embodiment and can be coupled to an audio, visual or audiovisual alarm that alerts the patient when the power supply needs to be recharged or replaced.

In the embodiment illustrated in FIG. 4, remote wireless communicator or transceiver 46 communicates with instrument communicator 48 via an RF signal 58. Signal 58 can be any of the following types: an electrical signal, a radio frequency signal, a microwave signal, a continuous signal, an intermittent signal, a signal sent only upon the sensing of the change and any suitable combination thereof. FIG. 3 shows that in an embodiment signal 58 is a continuous e.g., digitalized, data stream, which CPU 50 (via RAM 42 and DSP 44 and associated functions located in machine 100) uses to determine blood flowrate, peak flowrate, pulsatile characteristics of the blood flow, turbulence and the like. If an access disconnection occurs, the frequency of reflected ultrasonic waves 30*b* changes significantly enough as does the output of corresponding signal 58 that the software within buffering RAM 42 detects a partial or full access disconnection. When the access disconnection is detected, CPU 50 via signals 56 causes other components within machine 100 to take appropriate action, e.g., causes an audio, visual or audiovisual alarm to appear on and/or be sounded from graphical user interface 106 of machine 100. CPU also likely causes blood pump 102 to shut down.

In an alternative embodiment, the processing of reflected waves 30b is done on PCB 52. Here, onboard DSP 44 determines blood flowrate, peak flowrate, pulsatile characteristics of the blood flow, turbulence and the like. DSP 44 sends this information wirelessly via transceiver 46 to CPU 50 at predetermined intervals or when CPU 50 requests such information. When an access disconnection is detected, DSP via transceiver 46 sends an alarm signal 58 to CPU 50, which causes other components within instrument 100 to take appropriate action as described above. Thus wireless signal 58 can be a continuous signal, an intermittent signal or a signal sent only upon the sensing of the change and any suitable combination thereof.

In a further alternative embodiment, PCB 52 includes an audio, visual or audiovisual alarm, which alarms a patient of an access disconnection. In this embodiment, system 10 may or may not communicate with machine 100. For example, PCB 52 can sound an alarm, while machine 100 shuts down one ore more pump and occludes or closes one or more line or valve.

FIG. 5 illustrates schematically a test that has been performed using an ultrasound sensor, such as transducer 24 shown in FIG. 2, placed at the blood vessel of patient 12 downstream from venous needle 20 as also seen in FIG. 2. It should be appreciated that the systems described herein are operable with standard access needles 16 and 20 or with subclavian type catheters. As seen in FIG. 5, the patient's arm is modeled by a tube. The ultrasound sensor is placed over the tube. The patient's blood is modeled using saline, which an access pump pumps at approximately one liter per minute through a five hundred cubic centimeter compliance chamber, through tube (modeling the patient) and back into a source of the saline. Arterial and venous needles 16 and 20 shown schemtically in FIG. 5 are inserted or connected to the tube representing the patient's arm. The simulated extracorporeal circuit includes a blood pump, drip chamber, in combination with a pressure sensor, dialyzer and venous side pressure sensor.

FIG. 6 illustrates that when the venous access 20 was disloged from the tube, the ultrasound sensor noticed a discernable drop in flowrate of about 300 ml per minute. That is, the one liter per minute being pumped by the access pump in FIG. 5 returned at only 700 ml per minute as sensed by the ultrasound sensor.

Acoustic Access Disconnection Sensor

Figure 9:
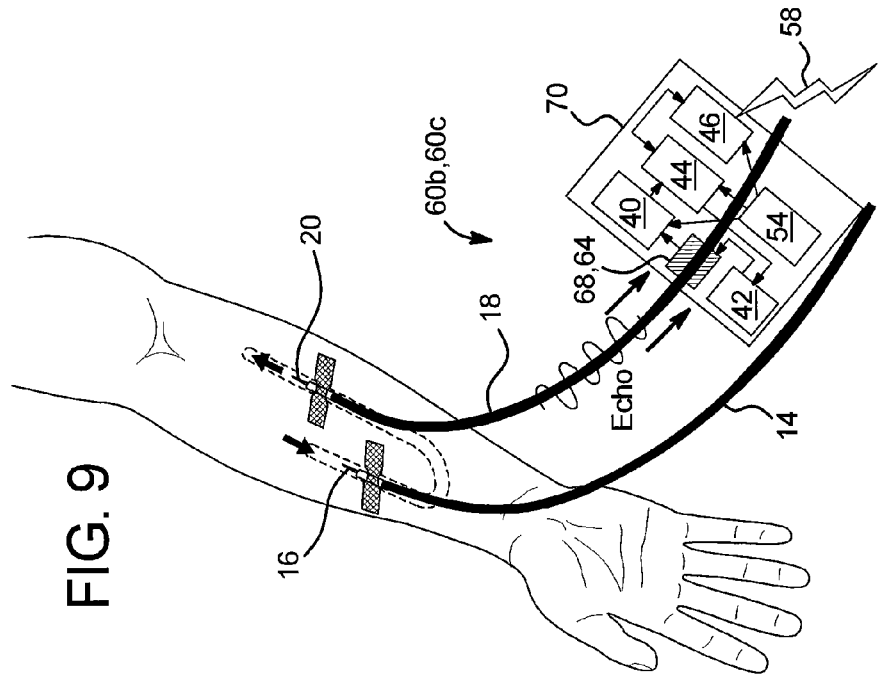
FIG. 9 is a perspective view showing either (i) a receive phase of the active sonar system of FIG. 8 or (ii) an alternative embodiment employing a passive sonar system, wherein both systems "listen" to either (i) an echo of the active transmitted signal or (ii) the acoustic signature of the extracorporeal circuit in the passive system.
Figure 8:
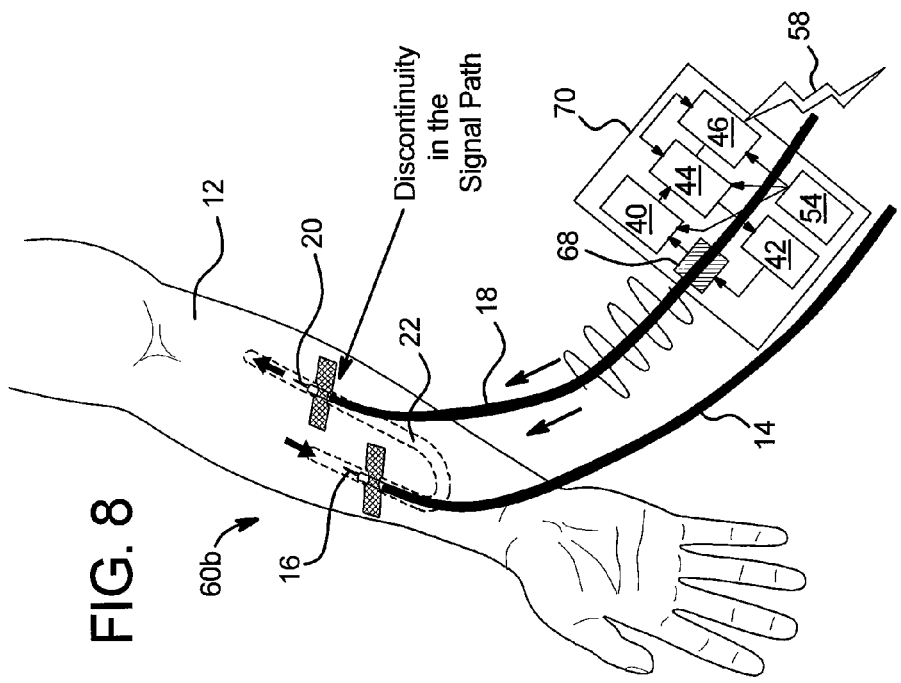
FIG. 8 is a perspective view showing an additional embodiment of an acoustic access disconnection system, which employs active sonar, and which is system is depicted in a transmit phase.

Referring now to FIGS. 7 to 9, various embodiments for acoustic access disconnection systems are illustrated by systems 60a to 60c (referred to herein collectively as acoustic access disconnection systems 60 or generally as acoustic access disconnection system 60). Access disconnection systems 60 have many similarities with ultrasound access disconnection system 10. Both are used with machine 100 (and each of its alternative configurations discussed above), have remote signaling capability, are non-invasive, do not circulate current through the patient's blood, do not add components to the disposable cassette or tubing set, saving cost, and have additional blood parameter measurement capability. Both systems 10 and 60 use sound waves.

One primary difference with systems 60 is that the transducers and associated electronics are coupled to the arterial and venous lines 14 and 18 instead of to patient 12. This configuration may be advantageous from the standpoint that a disconnection of one of the lines 14 and 18 should produce a relatively dramatic change in reflected waves. Additional blood parameter measurements will reflect blood flow characteristics in the extracorporeal circuit rather than blood flow characteristics in the patient as with system 10, which may be advantageous or disadvantageous.

Referring now to FIG. 7, a dual transducer transmit/receive acoustic access system 60a is illustrated. Acoustic access system 60a includes a printed circuit board 66, which carries transducers 62 and 64, signal conditioning 40, excitation apparatus 42, DSP 44 (including onboard memory) wireless transceiver 46 and power supply 54 described above. Power supply 54 as above powers excitation apparatus 42, DSP 44 and wireless transceiver 46, which operate as described above for system 10. DSP 44 communicates back and forth with remote transceiver 46, which communicates back and forth with machine transceiver 48. In an alternative embodiment, as with system 10 above, one or more of the apparatus and associated functionality of DSP 44 is located within machine 100. Machine 100 as before includes wireless, e.g., RF transceiver 48 to send and to receive signals 58 to and from wireless transceiver 46. Alternatively, machine 100 is hardwired to system 60a for electrical communication.

In the illustrated embodiment, acoustic emitter transducer 62 through excitation apparatus 42 transmits an acoustical signal into arterial line 14, while receiver transducer 64 receives an acoustical signal from venous line 18. Alternatively, emitter transducer 62 transmits an acoustical signal into venous line 18, while receiver transducer 64 receives an acoustical signal from arterial line 14. Tranducers 62 and 64 can be of a type in which each is constructed to be one of an emitter or a receiver. Alternatively, tranducers 62 and 64 are each both transmitters and receivers. Here, the roles of tranducers 62 and 64 upon an access disconnection event can be reversed to provide a redundant check. The roles of tranducers 62 and 64 can also be switched under normal operation to test that the transducers are working properly and also to provide redundancy for other parameters for which system 60a detects.

In an embodiment, tranducers 62 and 64 transmit and receive waves that are sonic, subsonic or pressure waves, for example, the signal can be sent in a single or in multiple frequencies. Transducer 62 can emit waves in a continuous, intermittent or pulsed manner. Further, the emitted signal can be modulated in any one or more combination of amplitude, frequency or phase. In a preferred embodiment, the signal is distinct from naturally occurring waves that receiver transducer 64 may also detect.

Excitation apparatus 42 excites acoustic emitter transducer 62 to emit sound waves in a direction towards patient 12. Acoustic receiver transducer 64 is likewise configured to receive sound waves from the patient. In this manner, the likelihood that sound waves will travel from emitter transducer 62, around blood pump 102, to receiver transducer 64 is minimized. Further, a drip chamber located in one or both of the arterial or venous lines provides an air barrier disconnect within the extracorporeal circuit, which should minimize sound wave coupling towards the blood pump. This directional configuration also maximizes the difference in signal reception when an access disconnection.

Signal conditioning 40 (e.g., an A/D converter) conditions the signal for DSP 44. It should be appreciated that the signal conditioning can be located alternatively within DSP 44. DSP 44 processes the conditioned signals using an onboard or a separate buffering RAM. DSP communicates with transceiver 46, which in turn sends and receives data from instrument transceiver 48. Transceiver 46 can alternatively be located onboard DSP 44. In any case, DSP 44 can be configured to detect a dislodgement by measuring a loss in power of the acoustic signal during disconnection. DSP 44 could also calculate blood flowrate, peak flowrate and any of the other parameters discussed herein.

If either arterial line 14 or venous line 18 becomes partially or completely disloged from patient 12, communication between tranducers 62 and 64 is broken or altered significantly enough that an access disconnection determination is made and any of the protective actions discussed herein, e.g., alarm, pump shutdown, valve closing, line occluding is carried out. In the illustrated embodiment, the processing of the breaking or interruption of communication between tranducers 62 and 64 is done on PCB 66. Here, under normal operation, PCB 66 determines the power and frequency of the received signal, and potentially, blood flowrate, peak flowrate, pulsatile characteristics of the blood flow, turbulence and the like as described above. This information is sent wirelessly via transceiver 46 to CPU 50 of instrument 100 on a continuous basis, at predetermined intervals, or when CPU 50 requests such information. When an access disconnection is detected, DSP via emitter 46 sends an alarm signal 58 to CPU 50, which causes other components within machine 100 to take appropriate action as described above. The wireless signal 58 can accordingly be a continuous signal, an intermittent signal, a signal sent only upon the sensing of the change and any suitable combination thereof.

In an alternative embodiment, the various components of PCB 66 are provided in machine 100 such as DSP 44. Here, the RF signal 58 is a continuous data stream, which can be conditioned e.g., digitized, locally and sent to CPU 50 of machine 100. DSP 44 now within instrument 100 uses data stream 58 to determine the power and frequency of the received signal, and potentially, blood flowrate, peak flowrate, pulsatile characteristics of the blood flow, turbulence and the like within machine 100. If an access disconnection occurs, the data contained in the RF signal 58 changes enough so that the software within instrument 100 detects a partial or full access disconnection. When the access disconnection is detected, CPU 50 causes, e.g., through a delegate controller, other components within machine 100 to take appropriate protective action as described above.

In a further alternative embodiment, PCB 66 includes an audio, visual or audiovisual alarm, which alarms a patient of an access disconnection. In this embodiment, system 10 may or may not communicate with machine 100.

Referring now to FIGS. 8 and 9, an active sonar or echo system 60b employs either a single acoustic transducer 68, doubling as transmitter and receiver (as illustrated), or dual transducers, one emitting and one receiving. In either case, the single or dual transducers are coupled to a single one of the extracorporeal lines, e.g., venous line 18 in one preferred embodiment (as described above venous access dislodgment is potentially more dangerous than arterial access dislodgement).

Active sonar or echo system 60b includes a printed circuit board 70, which carries signal conditioning 40, excitation apparatus 42, DSP 44, wireless remote transceiver 46 and power supply 54 described above. Power supply 54 powers signal conditioning 40, DSP 44 and transceiver 46. In an alternative embodiment, as with system 10 above, one DSP 44 is located within machine 100. Machine 100 as before inlcudes wireless, e.g., RF, transceiver 48 to receive signals from RF emitter 46. Alternatively, machine 100 is hardwired to system 60b for electrical communication.

In the illustrated embodiment, acoustic emitter transducer 68 transmits an acoustical signal into the blood of venous line 18. The signal reflects in the extracorporeal circuit lines 14, 18 and graft 22, producing a signature response. Signal conditioning 40 processes the signature response, e.g., digitizes it, and sends a digital signal to DSP 44 (which can include RAM, ROM, onboard signal conditioning and/or onboard transceiver) located either locally at PCB 70 or at machine 100. DSP 44 analyzes the signal using onboard software in one embodiment. DSP 44 formulates a baseline acoustic signature of the reflected acoustical wave and stores such baseline signal in RAM 42.

Acoustic emitter/receiver transducer 68 is configured to emit sound waves in a direction towards patient 12. Transducer 68 is likewise configured to receive sound waves from the patient. The likelihood that sound waves will travel from transducer 68, around blood pump 102, back to transducer 68 is minimal due at least in part to a drip chamber that is located between the transducer and the blood pump in the arterial blood line. This directional configuration also maximizes the difference in signal reception when an access disconnection occurs.

If either arterial line 14 or venous line 18 becomes partially or completely disloged from patient 12, the signature response back to transducer 68 is broken or altered significantly enough compared to the baseline acoustic signature, that an access disconnection determination is made and any of the actions discussed herein is performed, e.g., alarm, pump shutdown, valve closing, line occluding.

In the illustrated embodiment, the processing of the difference between the received response and the baseline response is done at PCB 70. Here, under normal operation, onboard DSP 44 determines the power, frequency and shape of the envelope of the received signal, and potentially, blood flowrate, peak flowrate, pulsatile characteristics of the blood flow, turbulence and the like. This information is sent wirelessly via DSP 44 and communicator 46 to CPU 50 continuously, at predetermined intervals, or when CPU 50 requests such information. When an access disconnection is detected, DSP 44 via communicator 46 sends an alarm signal to CPU 50, which causes other components within machine 100 to take appropriate action as described above. The wireless signal can accordingly be a continuous signal, an intermittent signal, a signal sent only upon the sensing of the change and any suitable combination thereof.

In an alternative embodiment, the majority of the components of PCB 70 are provided in machine 100. Here, the RF signal 58 is a continuous data stream, which can be conditioned, e.g., digitized, locally and sent to the CPU of machine 100, which operates with DSP 44 and their associated functions. Data stream 58 is used to determine blood flowrate, peak flowrate, pulsatile characteristics of the blood flow, turbulence and the like within machine 100. If an access disconnection occurs, the RF signal 58 is interrupted or is otherwise reduced enough that the software within buffering DSP 44 detects a partial or full access disconnection. When the access disconnection is detected, CPU 50 causes other components within machine 100 to take appropriate action as described herein.

In a further alternative embodiment, PCB 70 includes an audio, visual or audiovisual alarm, which alarms a patient of an access disconnection. In this embodiment, system 10 may or may not communicate with machine 100.

Referring again to FIG. 9, a passive sonar or acoustic signature system 60c employs a single receiver transducer 64. Transducer 64 is coupled to a single one of the extracorporeal lines, e.g., venous line 18 in one preferred embodiment (as described above venous access dislodgment is potentially more dangerous than an arterial access dislodgement).

Passive sonar or acoustic signature system 60c includes printed circuit board 70, which carries signal conditioning 40, excitation apparatus 42, DSP 44, wireless communicator 46 and power supply 54 described above. In an alternative embodiment, as with the systems above, one or more of the apparatuses and associated functionality of DSP 44 is located within machine 100.

Passive sonar system 60c uses pulses generated by the system's blood pump, drip chamber, interaction with the dialyzer or other extracorporeal device. These devices create an acoustical pattern or signature response at receiver transducer 64, similar to the signature response discussed above. Signal conditioning 40 processes the signature response, e.g., digitalizes it, and sends a digital signal to DSP 44, located either locally at PCB 70 or at machine 100. DSP 44 analyzes the signal using onboard software in one embodiment. DSP 44 formulates a baseline acoustic signature of the reflected acoustical wave and stores such baseline signal in memory.

If in the illustrated embodiment, venous line 18 becomes partially or completely disloged from patient 12, the signature response back to transducer 68 is broken or altered significantly enough compared to the baseline acoustic signature, that an access disconnection determination is made. Any of the actions discussed herein is then performed, e.g., alarm, pump shutdown, valve closing, line occluding is carried out.

In the illustrated embodiment, the processing of the difference between the received response and the baseline response is done on PCB 70 of system 60c. Here again, under normal operation, onboard DSP 44 determines blood flowrate, peak flowrate, pulsatile characteristics of the blood flow, turbulence and the like. This information is sent wirelessly via DSP 44 and transceiver 46 to CPU 50 continuously, at predetermined intervals, or when CPU 50 requests such information. When an access disconnection is detected, DSP via transceiver 46 sends an alarm signal to CPU 50, which causes other components within machine 100 to take appropriate action as described herein.

In an alternative embodiment, DSP 44 is provided in machine 100. Here, the RF signal 58 is a continuous data stream, which can be conditioned, e.g., digitized, locally and sent to the CPU of machine 100 via RF communication. Again, data stream 58 can be used to determine blood flowrate, peak flowrate, pulsatile characteristics of the blood flow, turbulence and the like within machine 100. If an access disconnection occurs, the RF signal 58 is interrupted or is otherwise reduced enough that the software within buffering DSP 44 detects a partial or full access disconnection. When an access disconnection is detected, CPU 50 causes, e.g., via a delegate controller, other components within machine 100 to take appropriate protective action as described above.

In a further alternative embodiment, PCB 70 of system 60c includes an audio, visual or audiovisual alarm, which alarms a patient of an access disconnection. In this embodiment, system 10 may or may not communicate with machine 100.

Optical Access Disconnection/Blood Leak Detector

Referring now to FIGS. 10 to 14, an embodiment of an optical access disconnection/blood leak detection system 80 is illustrated. Optical access disconnection/blood leak detection system 80 takes advantage of the gauze that is normally applied to patient 12 over access needles 16 and 20. It is not uncommon that under normal operation a small leak is present around the access points in which needles 16 and 20 connect to patient's arm 12. The normal blood leakage however should be limited to a small area around access needles 16 and 20. If the blood leak extends to a larger area, it likely indicates a needle dislodgement that needs to be addressed immediately.

Figure 10:
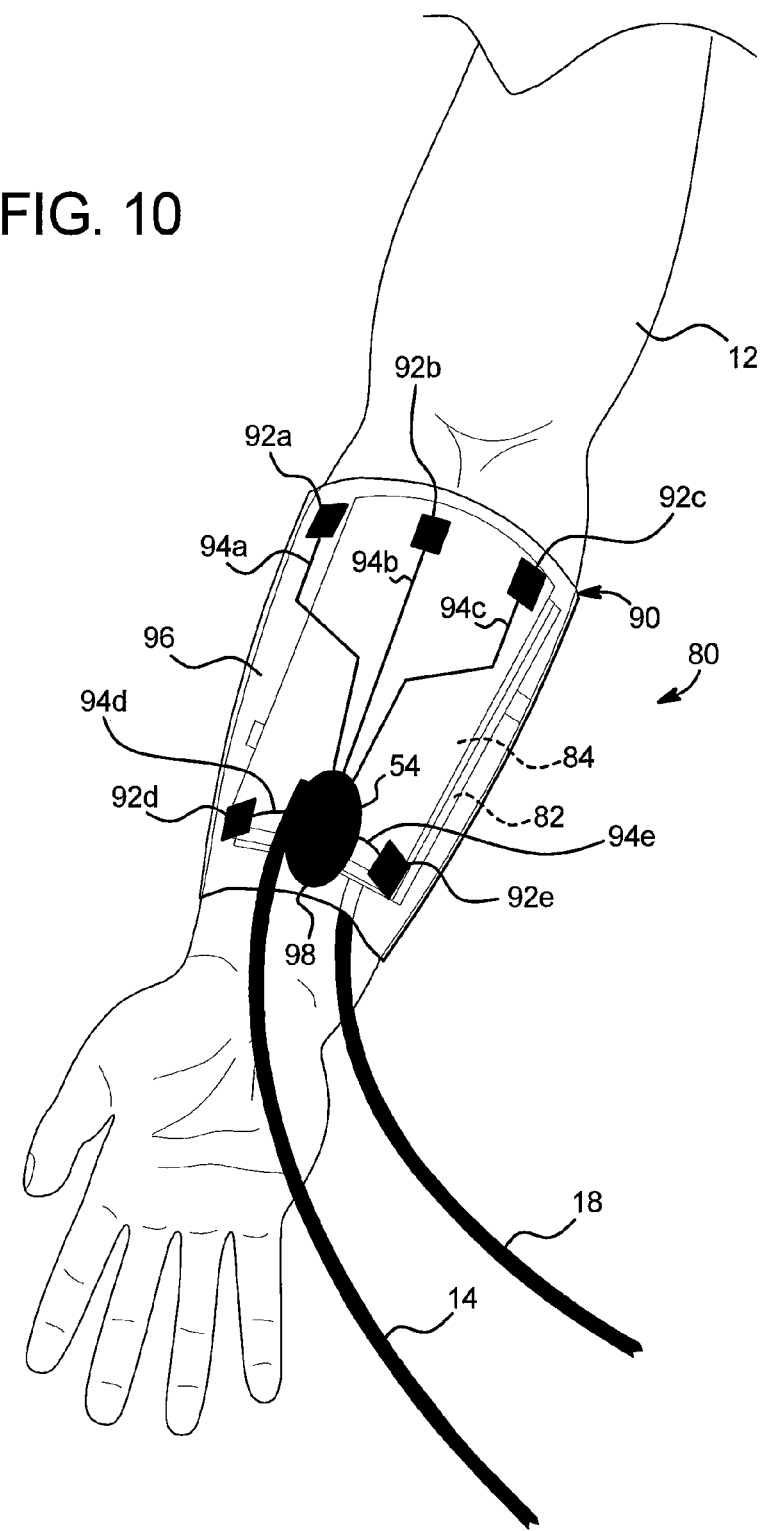
FIG. 10 is a perspective view showing one embodiment of an optical access disconnection system.

FIG. 10 illustrates that optical access disconnection/blood leak detection system 80 provides a flexible circuit 90. Flexible circuit 90 wraps around arm 12 of the patient. In an embodiment, flexible circuit 90 is placed over the gauze pad 82 shown in FIG. 10, which as mentioned is placed over access needles 16 and 20. Because the flex circuit 90 contacts gauze 82, sterility needs to be considered. In one embodiment, flexible circuit 90 is cleaned with a disinfectant prior to being placed over gauze 82. In an alternative embodiment, gauze 82 is covered with a sterile disposable film 84, which can be self-adhesive. Here, film 84 is discarded after treatment is completed. Film 84, isolates flexible circuit 90 from the contact area.

Arm band system 90 provides preventive action against needle dislodgement. By wrapping around the needles and tubing, flexible circuit 90 secures the needles and tubing in position and accordingly tends to prevent dislodgement. Arm band system 90 confines the connections between the fistulas and associated tubing to an area covered by flexible circuit 90, so that the system can also detect a disconnection between the fistula and the tubing.

Figure 11:
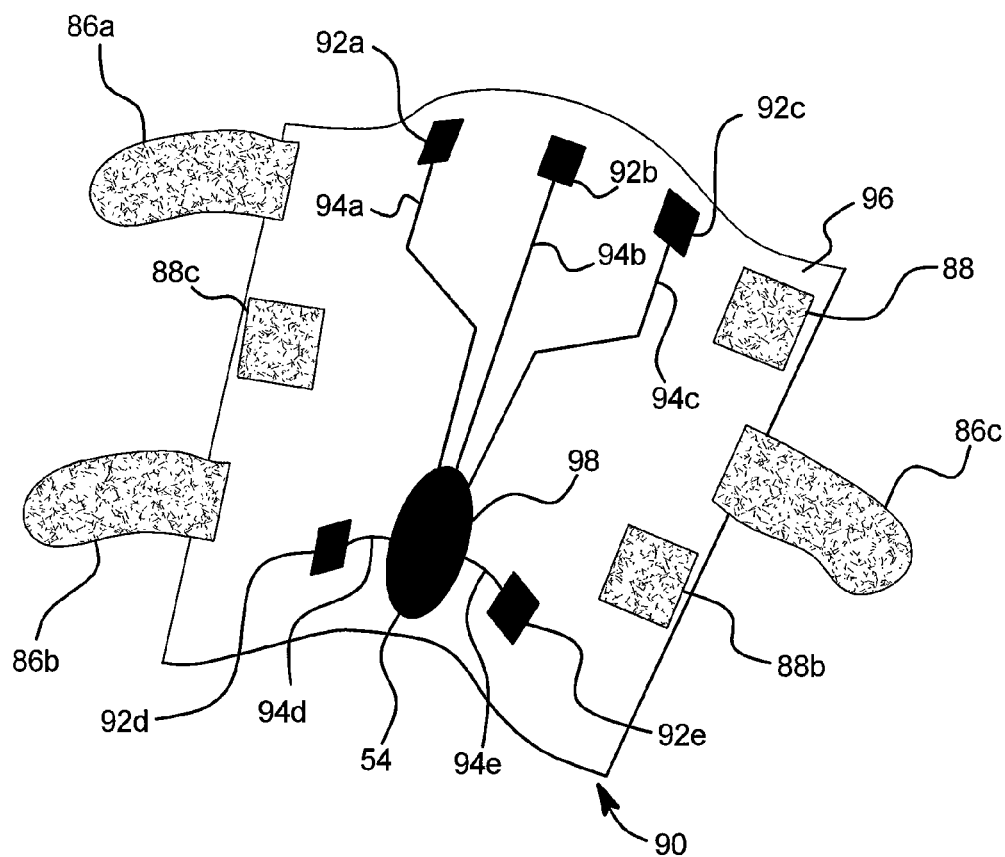
FIG. 11 is a perspective view showing one embodiment of a flexible circuit used with the optical access disconnection system of FIG. 10.

FIG. 11 illustrates that flexible circuit 90 in one embodiment includes hooks 86a to 86c, which loop around flex circuit 90 and attach, e.g., frictionally and/or adhesively, to mating pads 88a to 88c, respectively. For example, hooks 86 (referring collectively to hooks 86a to 86c) can attach to pads 88 (referring collectively to pads 88a to 88c) via a Velcro™ type attachment, buttons, slits, folds or other types of releasably securable mechanisms. If it is found that hooks 86 and pads 88 are difficult to clean, they can be replaced in one embodiment with a more hygienic attach mechanism, such as magnetic straps and buckles.

As seen in FIGS. 10 and 11, flexible circuit 90 includes a plurality of reflective photo sensors 92a to 92e, which are each powered via leads 94a to 94e, respectively, connecting to a power source 54, such as a coin battery. Optical sensors 92 (referring collectively to sensors 92a to 92e) in an embodiment include a light emitting diode ("LED") acting as the light source, and a photocell or phototransistor, acting as a light receiver. The LED and photosensor are configured for a specific wavelength that allows maximum absorption when reflected in blood. LED/Photosensor combinations such as ones used in hemodialysis blood leak detectors have been used successfully in a prototype of optical system 80.

Leads 94 (referring collectively to leads 94a to 94d) in an embodiment are trace, e.g., copper traces, that are applied in a known process to flexible circuit 90. In an embodiment, flexible circuit 90 uses an electrically insulative material, such as a polyamide or Kapton™ film 96. Film 96 in an embodiment is provided in multiple plies, with leads 94 and photosensors 92 sandwiched between the multiple pliers 96.

Power supply 54 in an embodiment is also sandwiched between the multiple dielectric films 96. Power supply 54 in one embodiment also powers a microcontroller 98, which can include any one or more of signal conditioning 40, RAM 52, DSP 44 and RF emitter 46 described previously herein. Microcontroller 98 can also include an audible alarm and/or a video status indicator, such as an LED, which signals whether electronics of optical access disconnection/blood leak detection system 80 are performing properly.

Figure 13:
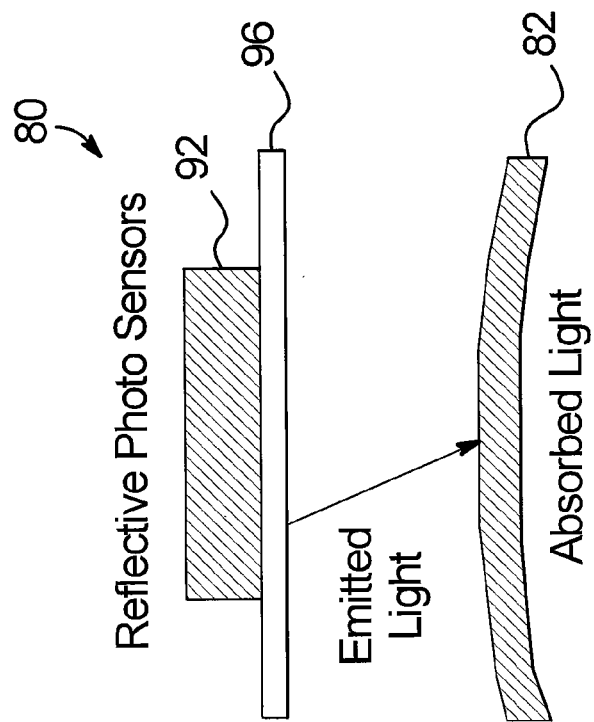
FIG. 13 is a schematic elevation view representing the optical access disconnection system of FIG. 10 in an access disconnection state.
Figure 12:
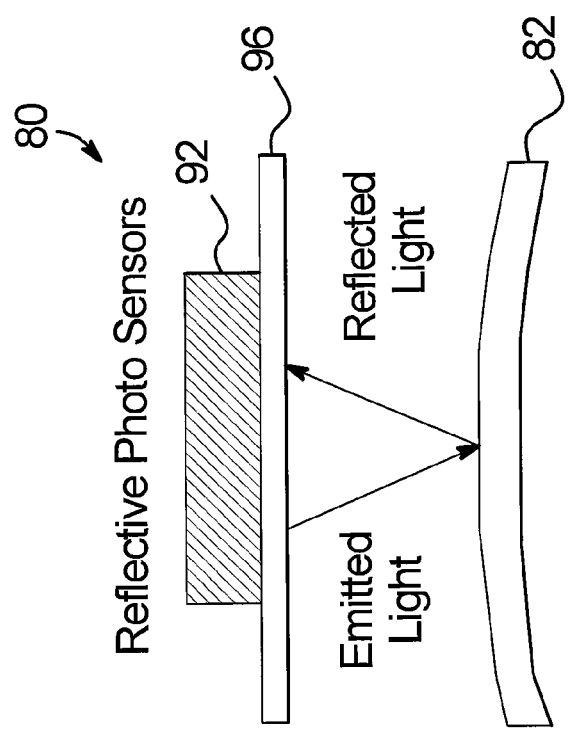
FIG. 12 is a schematic elevation view representing the optical access disconnection system of FIG. 10 in a normal state.
Figure 14:
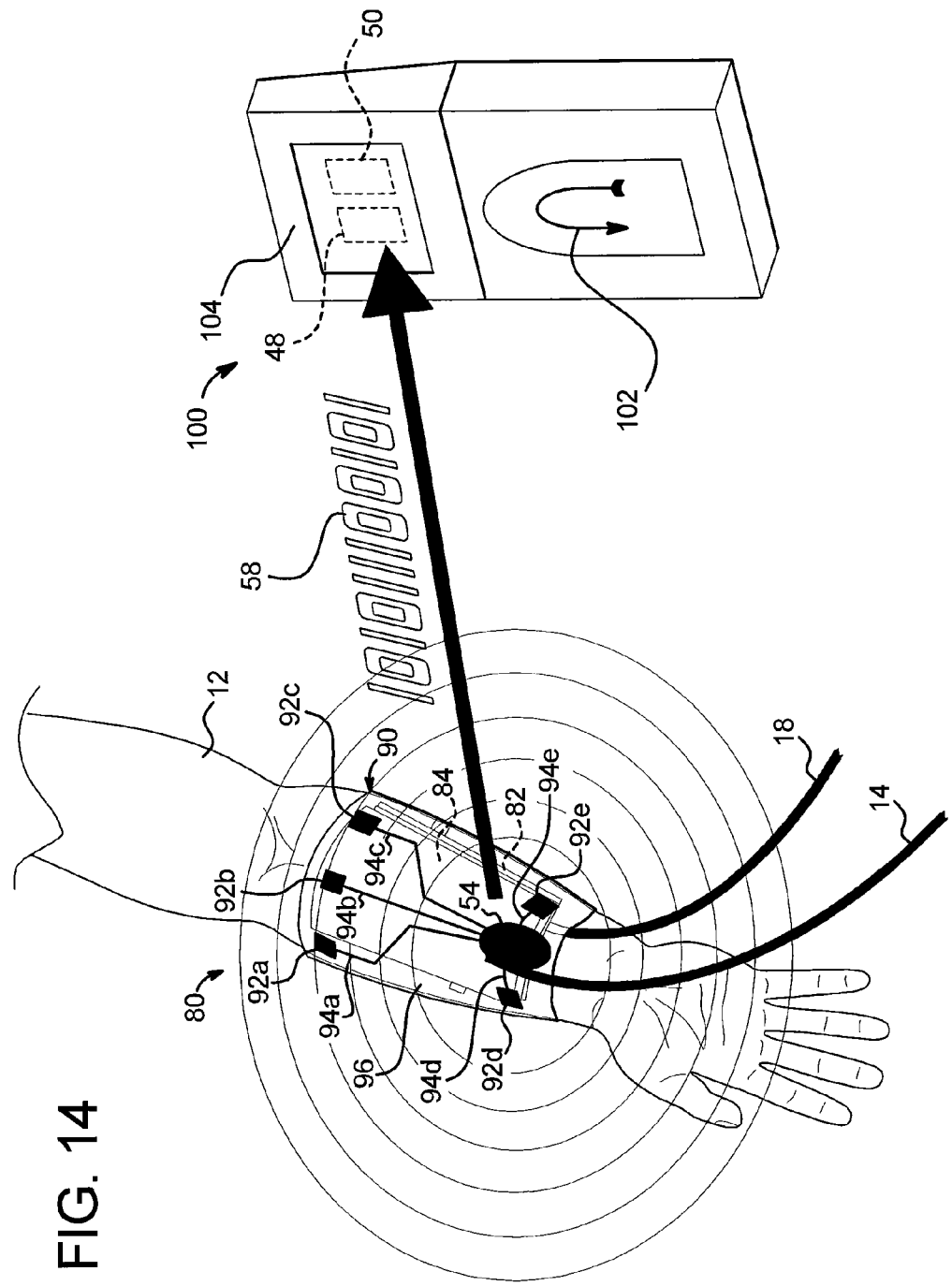
FIG. 14 is a perspective view showing the optical system of FIG. 10 and one embodiment for it to communicate with a blood treatment machine.

FIGS. 12 and 13 illustrate one embodiment for operating photoelectric system 80. In an embodiment, light emitted from the LED of photosensor 92 has a wave length for example in the range of the blue to green of the ultraviolet wave spectrum, which is absorbed by the color of blood collected on gauze 82. When light from sensor 92 illuminates non-bloodied or white gauze 82 shown in FIG. 12, a percentage of its energy reflects towards a receiver, e.g., photocell or phototransistor, of photosensor 92. In FIG. 13 on the other hand, the presence of blood on gauze 82 absorbs most of all light energy emitted from sensor 92, such that sensor 92 receives and detects considerably less light, e.g., a loss of signal. Accordingly, in FIG. 13 the arrow from gauze 82 back to photosensor 92 indicating reflected light is not shown.

In the embodiment illustrated in FIG. 11, sensors 92*a* to 92*e* are spaced a relatively far distance from access needles 16 and 20, e.g., on the order of one inch to three inches from the needles, such that if blood reaches sensors 92, it has traveled a distance sufficient from the access points to signal an access disconnection rather than a normal amount of blood leakage. Further, using multiple sensors 92*a* to 92*e* allows redundancy to be built into the software, in which for example the software looks for multiple ones of sensors 92 to show a lack of reflection before determining that an access disconnection has occurred. Alternatively, a single sensor 92 sensing blood can be taken to indicate an access disconnection.

In one implementation, two or more concentric rings of optical sensors of different diameters form a sensor array that allows the system to monitor the progress of a blood leak. One of the sensors of the internal ring (small diameter sensors) looks for a lack of reflection that, due to the sensor's small diameter, is considered insignificant. If the next ring of (larger diameter) sensors does not lose reflected light, the system determines that the leak is not serious. Should the leak become serious, it reaches the outer ring of larger diameter sensors. The system uses the time between detections in successive rings to determine the flow of the blood leakage. The spacing between rings allows estimation of the volume of blood leakage.

Microcontroller 98 gathers data from optical sensors 92 and reports this data in an embodiment via RF signal 58 to dialysis machine 100. Machine 100 can include at least one of signal conditioning 40, DSP 44 (which can have onboard RAM and ROM as well as other apparatus and functionality as described herein), which are used to analyze signal 58. In an alternative embodiment, microcontroller 98 includes signal conditioning, such as an analog to digital converter and/or signal summing circuitry, which can combine the outputs from each of the photosensors 92 to yield a single digitized signal 58, which is representative of entire flex circuit 90. In a further alternative embodiment, the software and processing is stored in microcontroller 98, in which case signal 58 tells the machine 100 whether or not an access disconnection takes place. Again, signal 58 can be continuous, intermittent, sent only when commanded, etc.

To save the power of supply 54, microcontroller 98 in one embodiment is maintained in a sleeve or power save mode and optical sensors 92 are off until dialysis instrument 100 requests data from the radio frequency link. At this point, microcontroller 98 "wakes up", energizes light sensors 92, reads signals from optical receivers of sensors 92 and transmits status information back to dialysis instrument 100. In one embodiment, again, if any of sensors 92*a* to 92*e* does not receive enough light, DSP 94 issues a distress call to machine 100 and simultaneously energizes an audio alarm. Machine 100 can cause any other suitable protective action described herein to be taken.

Electrocardiogram ("ECG") Remote Access Disconnection Sensor

Referring now to FIGS. 15, 16, 17 and 18A to 18C, various systems are shown that detect an access disconnection using signals form an electrocardiogram ("ECG"). Generally, an ECG is a test that measures electrical signals that control the rhythm of a person's heartbeat. The heart is a muscular pump made up of four chambers, two upper chambers called atria and two lower chambers are called ventricles. A natural electrical system causes the heart muscle to contract and pump blood through the heart to the lungs and the rest of the body.

Electrodes for the ECG are placed on a patient's skin to detect this natural electrical activity of the heart. In system 120 of FIG. 15, during dialysis therapy, a first electrode 122 is attached to venous line 18, while a second electrode 124 is attached to the patient's skin, for example, at leg 12*a* (as shown here), arm 12*b*, or chest 12*c* of patient 12 or is alternatively connected to arterial line 14. Electrodes 122 and 124 can be connected at venous line 18 and arterial line 14 through direct contact, capacitive coupling, inductive coupling, wireless or otherwise. Alternatively, multiple body electrodes 124 can be placed at different locations 12*a*, 12*b*, 12*c* of patient 12.

FIGS. 18A to 18C show three possible arrangements for contact/blood coupling. In FIG. 18A, electrode 122 is placed inside venous line 18 and contacts blood directly. In FIG. 18B, electrode 122 is embedded within the wall of venous line 18 and couples to the blood, e.g., capacitively or inductively. In FIG. 18C, electrode 122 is placed outside of venous line 18 and likewise couples to the blood, e.g., capacitively or inductively. The electrodes can be metal or of a conductive polymer material.

Figure 15:
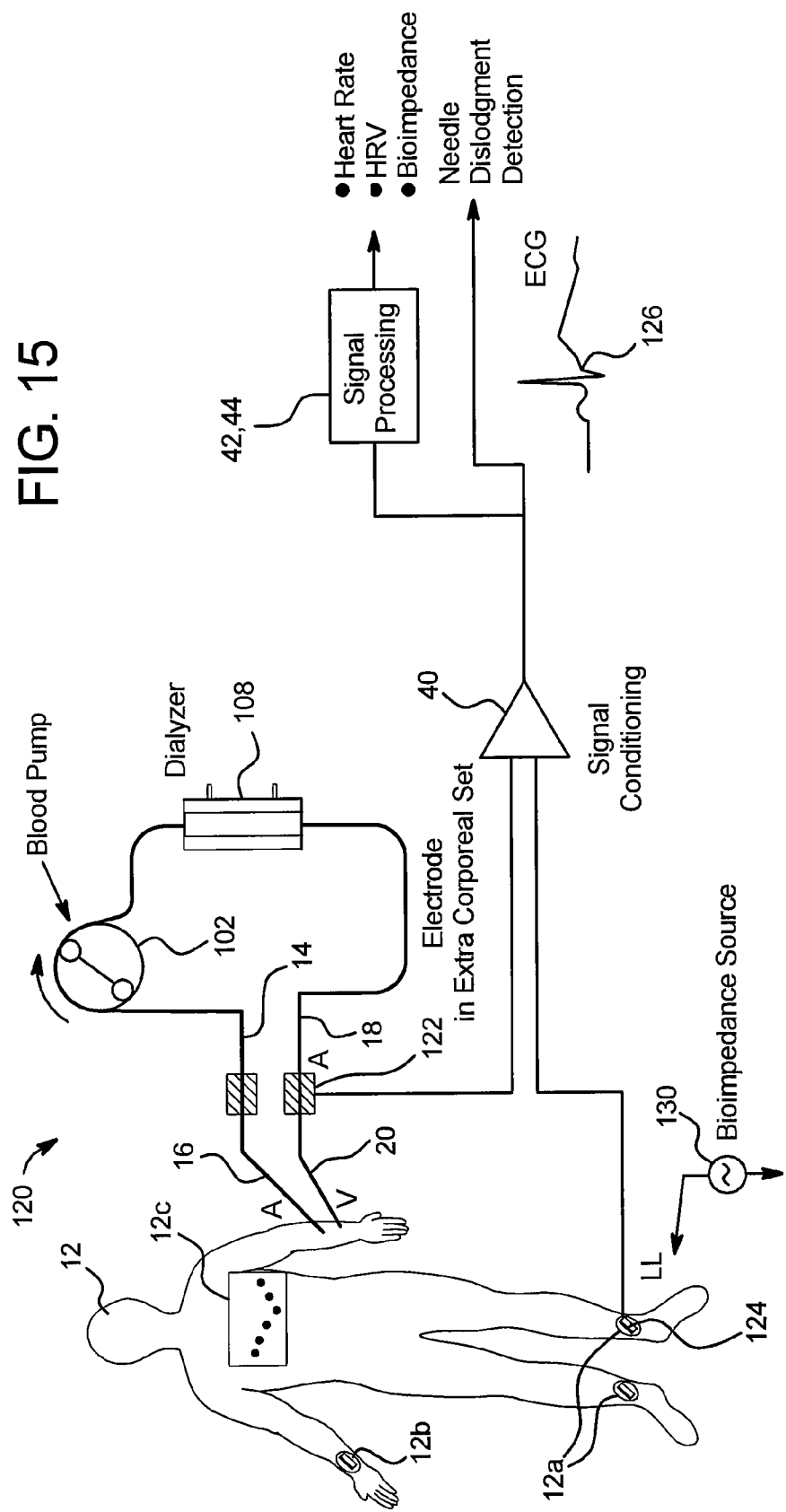
FIG. 15 is a schematic view of one embodiment of a system that uses electrocardiogram ("ECG") signals to detect an access disconnection.

System 120 of FIG. 15 shows a blood pump 102 and dialyzer 108 connected to arterial line 14 and venous line 18. The extracorporeal circuit includes other components not illustrated here for convenience. Also, dialyzer 108 communicates with a dialysate source, e.g., bagged or on-line, an pumps that deliver dialysate to the dialyzer 108, which again are not shown for convenience. The '454 Patent referenced above discloses further details concerning the extracorporeal and dialysate circuits, which are applicable to each of the systems described herein. The teachings of each of the systems described herein are also applicable to access disconnection in hemofiltration and hemodiafiltration systems.

Electrodes 122 and 124 are connected electrically to signal conditioning 40 and signal processing, which can include RAM 42 and DSP 44 as has been discussed herein. Any of signal conditioning 40, RAM 42 and DSP 44 can be located locally or remotely as desired and as discussed herein.

Electrodes 122 and 124 can alternatively or additionally be connected to a machine that translates the electrical activity into an electrocardiogram, which may show: evidence of heart enlargement, signs of insufficient blood flow to the heart, signs of a new or previous injury to the heart (e.g., due to a heart attack), heart rhythm problems (arrhythmias), changes in the electrical activity of the heart caused by an electrolyte imbalance in the body, and signs of inflammation of the sac surrounding the heart (pericarditis). These parameters may be useful during dialysis as discussed in more detail below.

Under normal conditions, the natural electrical signals that control the rhythm of a person's heartbeat create a signal 126 shown figuratively in FIG. 15. Upon an access disconnection of venous line 18 in the illustrated embodiment, signal 126 is no longer sensed because electrical communication with the body through the blood is lost. Machine 100 sees the lack of signal 126 as an access disconnection and causes any of the measures discussed herein to be taken.

FIGS. 16 and 17 illustrate an alternative system 140 and catheter assembly 142 used in system 140, respectively. In system 140 of FIG. 16, a cardiac catheter access at chest 12*c* of patient 12 using cardiac catheter assembly 142 is used. Cardiac access and catheter assembly 142 provide a more direct access to the heart and its associated signals than does needle access at the arm 126 of patient 12. Cardiac access and catheter assembly 142 may be better suited for acute treatments. Here, the doctor can more directly monitor electrograms from the blood pool inside the heart and provide more or better information about the cardiac function than with typical arterial and venous access, while still dialyzing patient 12.

Catheter 146 of assembly 142 is equipped with electrodes, such as electrodes 122 and 124, via any of the configurations shown in connection with FIGS. 18A to 18C. Catheter assembly 142 includes an arterial access section 114 and a venous access section 118, which connect respectively to arterial line 14 and venous line 18 of the extracorporeal circuit. Catheter assembly 142 also includes a guide wire 144 for directing catheter 146 to a desired location, e.g., directly into the patient's heart or to a desired local vein, artery or graft.

In systems 120 and 140, signal processing via DSP 44 additionally or alternatively processes signal 126 to calculate any one or more of heart rate variability, respiration, stroke volume, cardiac output and central blood volume. Further, a bioimpedance source 130 is connected to the patient, so that system 120 may make bioimpedance measurements. Additionally or alternatively, systems 120 and 140 allow for the injection of a solution into the extracorporeal circuit, which is used for pacing control for patients having implanted cardiac rhythm management devices (pacemakers). System 120 and 140 allow for key cardiovascular parameters to be monitored during dialysis, which may have beneficial effects on the dialysis therapy or be used for other purposes.

Bioimpedance in general is a measure of changes in the electrical conductivity of the thorax or heart. It can for example be a measure based on pulsatile blood volume changes in the aorta. Bioimpedance is relevant to the measurement of cardiac output and circulating blood volume.

In particular, thoracic electrical bioimpedance (also referred to as impedance cardiography) has been investigated as a noninvasive way to assess cardiac output and other cardiovascular functions. Changes in cardiac output are used to identify a change in the hemodynamic status of a patient or to ascertain the need for, or response to, treatment, e.g., for critically ill patients and patients at high risk for morbidity and mortality.

Thoracic bioimpedance has been investigated for a variety of indications, including, evaluation of the hemodynamics of patients with suspected or known cardiovascular disease, differentiation of cardiogenic from pulmonary causes of acute dyspnea, optimization of atrioventricular interval for patients with A/V sequential pacemakers, and optimization of drug therapy in patients with congestive heart failure.

Any of the above parameters may be monitored either in connection with dialysis or as an additional benefit of the treatment.

Capacitive Blood Leak Detection System

Figure 19A:
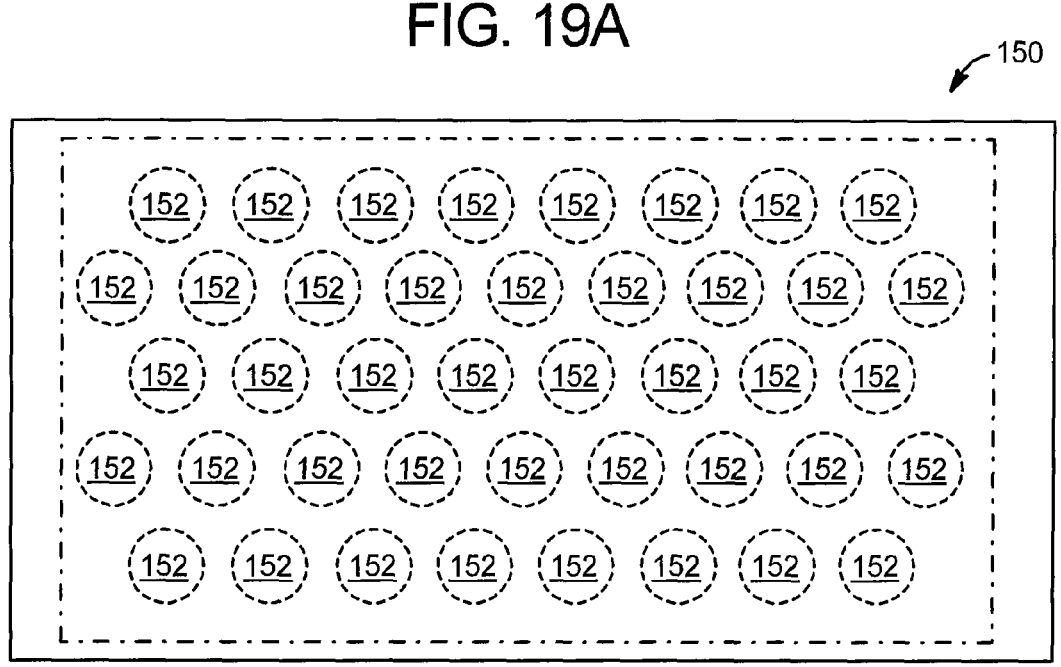
FIGS. 19A and 19B are top and side views of a capacitive sensing blood leak detection device.
Figure 19B:
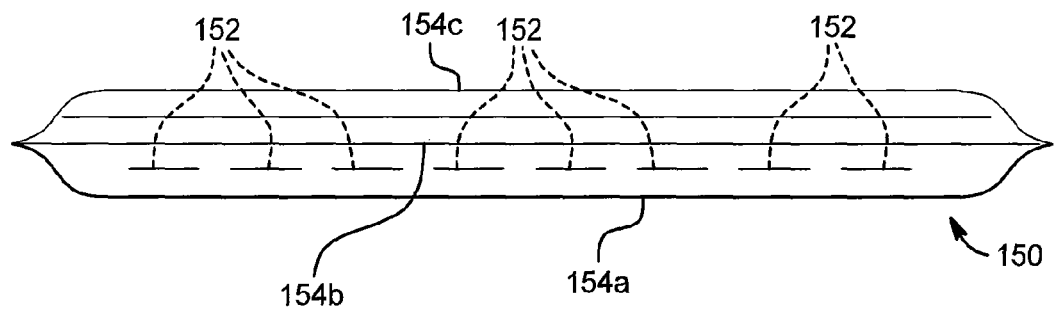

FIGS. 19A and 19B illustrate an alternative blood leak detection device 150, which wraps around a patient's arm in any of the manners discussed above with system 80 and covers access needles 16 and 20. Device 150 includes an array of mini-capacitors 152 as seen best in FIG. 19A. Waterproof, e.g., plastic, insulators 154a to 154c are placed around both sides of the capacitors. A ground or shield 156 is placed between the backside of capacitors 152 and rear insulator 154c.

Device 150 does not have to absorb blood to detect a blood leak. The presence of blood beneath mini-capacitors 152 results in a change in the dielectric field surrounding the capacitors. That is, if a wet spot develops beneath device 150, the region of capacitors 152 sensing a dielectric change would grow. If the region stops growing, the system using device 150 (which can be any of the remote or wired systems discussed herein) assumes a normal amount of seepage has occurred, which is distinguishable from a blood leak or needle dislodgement. A small amount of seepage is a common occurrence at "needle sticks" and should not produce an alarm. If the blood leak grows large enough, the system using device 110 assumes that a partial or full access disconnection has occurred and sounds an alarm.

Redundant Access Disconnection/Blood Leak Detection System

Certain known access disconnection systems rely on the breaking of an electrical circuit to detect an access problem. One problem with these systems is that a needle dislodging from the patient does not always break the electrical circuit. A needle can for example dislodge from the patient but direct the flow of blood over the access from which the needle has been dislodged or over the other (e.g., arterial) needle to complete or re-complete the electrical circuit. Here, blood would not be returned to the patient but no alarm would sound.

Other known systems assume that a dislodged needle will direct the flow of blood onto a part of the device or system. Here, if the needle is dislodged completely and quickly from under the device, the flow of blood that is supposed to seep onto a part of the system may not (or not enough) and again no alarm is sounded.

To address the above described problems, any of the above-described systems can be used in combination with one another or in combination with other types of access disconnection or blood leak detection systems. In particular, a dislodgement type system can be combined with a blood leak detection system. Optical system 80 for example is a blood leak detection system, which is particularly adept at detecting blood leaking at the access site. Another type of blood leak detection system is a conductive blanket or pad, which covers the access site in a manner similar to system 80 of FIGS. 10 to 14. The conductive blanket or pad includes contacts which form a closed electrical loop when contacted by blood seeping from the patient access. An additional blood leak detection system 150 is disclosed above in connection with FIGS. 19A and 19B.

Dislodgement systems, such as impedance sensing systems described in the '098 and '480 Patents discussed above, are particularly adept at detecting when a needle or other access instrument has become fully dislodged from the patient. Ultrasound access disconnection system 10, acoustic systems 60a to 60c and bioimpedance system 120 are also dislodgement type systems that adeptly detect a full needle dislodgement.

Accordingly, it is contemplated to combine one of each of the blood leak detection systems and needle dislodgement systems in a hybrid or redundant system, which adeptly detects either failure mode. For example, any one of the impedance systems of the '098 and '480 Patents, ultrasound access disconnection system 10, acoustic systems 60a to 60c and bioimpedance system 120 (fall dislodgement) can be combined with any one of the optical (system 80), conductive blanket or capacitive (device 150) blood leak detection systems, so that the manner in which the venous needle has been dislodged does not matter. The access disconnection system causes an alarm if the venous needle is dislodged quickly and falls off of the patient. The blood leak detection system causes an alarm if the venous needle is partially of fully dislodged and directs blood flow over the venous or arterial needle.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. An access disconnection system comprising:
    a material capable of absorbing blood from a patient upon an arterial or venous line disconnection;
    a plurality of light emitters positioned to emit light onto the material;
    a plurality of light receivers positioned to receive light reflected off of the material, the light receivers being positioned in a first ring having a first diameter and a second ring having a second diameter, the first and second rings being concentric, and the first diameter being smaller than the second diameter; and
    electronic circuitry operably coupled to the plurality of light emitters and receivers, the circuitry configured to provide: (i) a first output when the light receivers of the first ring detect that the received light reaches or passes a particular level and light receivers of the second ring detect that the received light does not reach the particular level, and (ii) a second output when the light receivers of the first and second rings both detect that the received light reaches or passes the particular level,
    and wherein the light receivers included within the first ring are positioned a d istance less than three inches (7.6 cm) from a portion of the material intended to cover the arterial line and venous line connections, such that the location that light is reflected off of the material provides for an allowable amount of blood seepage from the patient due to a needle stick.

2. The access disconnection system of claim 1, which includes an attachment mechanism operable to attach the material to an arm of the patient.

3. The access disconnection system of claim 1, wherein the light emitters emit light having a wavelength causing the light to be absorbed by blood.

4. The access disconnection system of claim 1, which includes at least one of : (i) the material being gauze; (ii) the light emitters being a light emitting diode; and (iii) the light receivers being a photocell or phototransistor.

5. The access disconnection system of claim 1, which includes a film positioned between the material and the light emitters/receivers, the material selected to allow light to pass through the material.

6. The access disconnection system of claim 1, wherein the electronic circuitry is configured to provide the first and second outputs when light received by the receivers fall to the particular level.

7. The access disconnection system of claim 1, wherein the particular level is an at least substantially no-light received level.

8. The access disconnection system of claim 1, wherein the first and second outputs are of a type selected from the group consisting of: an electrical output and a radio frequency output.

9. The access disconnection system of claim 1, which includes a blood treatment unit, the first and second outputs sent to the blood treatment unit.

10. The access disconnection system of claim 9, wherein the blood treatment unit performs at least one of: (i) determines if the amount of light received warrants an access disconnection condition; (ii) alarms the patient upon receiving the second output; and (iii) shuts down at least one of a blood pump and a dialysate pump upon receiving the second output.

11. The access disconnection system of claim 1, which includes a battery supply to at least one of the light emitters and light receivers.

12. The access disconnection system of claim 1, which is a redundant system that combines one of: (i) an electrical impedance access disconnection detector, (ii) an ultrasound access disconnection detector, (iii) an acoustic access disconnection detector and (iv) a bioimpedance access disconnection detector with the light emitters, light receivers and electronic circuitry.

13. An access disconnection system comprising:
    a material capable of absorbing blood from a patient upon an arterial or venous line disconnection;
    a plurality of light emitters positioned to emit light onto the material;
    a plurality of light receivers positioned to receive light reflected off of the material, the light receivers being positioned in a first ring having a first diameter and a second ring having a second diameter, the first and second rings being concentric, and the first diameter being smaller than the second diameter; and
    a flexible circuit including electronic circuitry operably coupled to at least one of the plurality of light emitters and light receivers, the circuitry configured to provide:
    (i) a first output when the light receivers of the first ring detect that the received light reaches or passes a particular level and light receivers of the second ring detect that the received light does not reach the particular level, and (ii) a second output when the light receivers of the first and second rings both detect that the received light reaches or passes the particular level,
    and wherein the plurality of light receivers included within the first ring are positioned peripherally along the flexible circuit, such that the location that light is reflected off of the material is a distance less than three inches (7.6 cm) from the arterial or venous line connection providing for an allowable amount of blood seepage from the patient due to a needle stick.

14. The access disconnection system of claim 13, wherein the electronic circuitry is configured to provide the access disconnection second output when light received by the at least one receiver falls to the particular level.

15. The access disconnection system of claim 13, which includes a blood treatment unit, the first and second outputs sent to the blood treatment unit.

16. The access disconnection system of claim 15, wherein the blood treatment unit performs at least one of: (i) determines if the amount of light received warrants an access disconnection condition; (ii) alarms the patient upon receiving the second output; and (iii) shuts down at least one of a blood pump and a dialysate pump upon receiving the second output.

17. The access disconnection system of claim 15, which is a redundant system that combines one of: (i) an electrical impedance access disconnection detector, (ii) an ultrasound access disconnection detector, (iii) an acoustic access disconnection detector and (iv) a bioimpedance access disconnection detector with the plurality of light emitters, plurality of light receivers and electronic circuitry.

18. The access disconnection system of claim 13, wherein the circuitry is configured to measure a time between the start of the first output and the start of the second output.

19. The access disconnection system of claim 12, wherein the plurality of light emitters are positioned in proximity to the plurality of light receivers in the first and second rings.

* * * * *

UNITED STATES PATENT AND TRADEMARK OFFICE
CERTIFICATE OF CORRECTION

PATENT NO.       : 8,376,978 B2  
APPLICATION NO.  : 11/673395  
DATED            : February 19, 2013  
INVENTOR(S)      : Roger et al.

Page 1 of 1

It is certified that error appears in the above-identified patent and that said Letters Patent is hereby corrected as shown below:

In the Claims:

In Claim 1, Column 17, Line 21, replace "recevivers" with -- receivers --.

In Claim 1, Column 17, Line 22, replace "ad istance" with -- a distance --.

Signed and Sealed this
Fourth Day of June, 2013

Teresa Stanek Rea
*Acting Director of the United States Patent and Trademark Office*

UNITED STATES PATENT AND TRADEMARK OFFICE
CERTIFICATE OF CORRECTION

PATENT NO. : 8,376,978 B2  
APPLICATION NO. : 11/673395  
DATED : February 19, 2013  
INVENTOR(S) : Roger et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1117 days.

Signed and Sealed this  
Sixteenth Day of December, 2014

Michelle K. Lee  
*Deputy Director of the United States Patent and Trademark Office*